(12) United States Patent
Lebovic et al.

(10) Patent No.: US 11,534,289 B2
(45) Date of Patent: Dec. 27, 2022

(54) IMPLANTABLE DEVICES AND TECHNIQUES FOR ONCOPLASTIC SURGERY

(71) Applicant: HOLOGIC, INC., Marlborough, MA (US)

(72) Inventors: Gail S. Lebovic, Frisco, TX (US); David B. Willis, Mountain View, CA (US); George D. Hermann, Los Altos Hills, CA (US); Jonathan M. Olson, San Jose, CA (US)

(73) Assignee: HOLOGIC, INC., Marlborough, MA (US)

( * ) Notice: Subject to any disclaimer, the term of this patent is extended or adjusted under 35 U.S.C. 154(b) by 514 days.

(21) Appl. No.: 16/518,139

(22) Filed: Jul. 22, 2019

(65) Prior Publication Data
US 2019/0336274 A1 Nov. 7, 2019

Related U.S. Application Data

(63) Continuation of application No. 15/456,030, filed on Mar. 10, 2017, now abandoned, which is a
(Continued)

(51) Int. Cl.
*A61F 2/12* (2006.01)
*A61B 17/00* (2006.01)
(Continued)

(52) U.S. Cl.
CPC ............. *A61F 2/12* (2013.01); *A61B 17/00* (2013.01); *A61B 17/0206* (2013.01);
(Continued)

(58) Field of Classification Search
CPC ............. A61F 2/12; A61F 2250/0068; A61F 2230/0013; A61B 2017/008
See application file for complete search history.

(56) References Cited

U.S. PATENT DOCUMENTS

| | | |
|---|---|---|
| 3,157,524 A | 11/1964 | Artandi |
| 3,520,402 A | 7/1970 | Nichols et al. |

(Continued)

FOREIGN PATENT DOCUMENTS

| | | | | |
|---|---|---|---|---|
| EP | 1997457 A1 | * 12/2008 | ............... | A61F 2/12 |
| JP | 2008515592 A | 5/2008 | | |

(Continued)

OTHER PUBLICATIONS

Bouman, Reconstruction of the breast after subcutaneous mastectomy. Possibilities and problems, 1974, Archivum Chirurgicum Neerlandicum, 26, 4:343-352 (Year: 1974).*

(Continued)

*Primary Examiner* — Brian E Pellegrino
(74) *Attorney, Agent, or Firm* — Jones Robb, PLLC

(57) ABSTRACT

Described herein are devices for placement in surgically created soft tissue spaces, potential spaces, or cavities. The implantable devices generally include a bioabsorbable body having an open framework that facilitates attachment of tissue thereto in a manner that helps avoid post-surgical deformities. Methods for using the implantable devices in oncoplastic surgery are further described.

25 Claims, 19 Drawing Sheets

Related U.S. Application Data continuation of application No. 14/808,852, filed on Jul. 24, 2015, now Pat. No. 9,615,915.

(60) Provisional application No. 62/029,358, filed on Jul. 25, 2014.

(51) Int. Cl.
*A61B 90/00* (2016.01)
*A61B 17/02* (2006.01)

(52) U.S. Cl.
CPC . *A61B 2017/008* (2013.01); *A61B 2090/3908* (2016.02); *A61F 2210/0004* (2013.01); *A61F 2230/0008* (2013.01); *A61F 2230/0013* (2013.01); *A61F 2230/0076* (2013.01); *A61F 2230/0091* (2013.01); *A61F 2250/0059* (2013.01); *A61F 2250/0068* (2013.01); *A61F 2250/0097* (2013.01); *A61F 2250/0098* (2013.01)

(56) References Cited

U.S. PATENT DOCUMENTS

| | | |
|---|---|---|
| 4,298,998 A | 11/1981 | Naficy |
| 4,832,686 A | 5/1989 | Anderson |
| 4,957,479 A | 9/1990 | Roemer |
| 5,019,087 A | 5/1991 | Nichols |
| 5,429,582 A | 7/1995 | Williams |
| 5,607,477 A | 3/1997 | Schindler et al. |
| 5,626,611 A | 5/1997 | Liu et al. |
| 5,676,146 A | 10/1997 | Scarborough |
| 5,716,404 A | 2/1998 | Vacanti et al. |
| 5,873,865 A | 2/1999 | Horzewski et al. |
| 6,030,333 A | 2/2000 | Sioshansi et al. |
| 6,071,301 A | 6/2000 | Cragg et al. |
| 6,080,099 A | 6/2000 | Slater et al. |
| 6,159,165 A | 12/2000 | Ferrera et al. |
| 6,161,034 A | 12/2000 | Burbank et al. |
| 6,174,330 B1 | 1/2001 | Stinson |
| 6,203,570 B1 | 3/2001 | Baeke |
| 6,214,045 B1 | 4/2001 | Corbitt, Jr. et al. |
| 6,228,055 B1 | 5/2001 | Foerster et al. |
| 6,245,103 B1 | 6/2001 | Stinson |
| 6,270,464 B1 | 8/2001 | Fulton, III et al. |
| 6,340,367 B1 | 1/2002 | Stinson et al. |
| 6,356,782 B1 | 3/2002 | Sirimanne et al. |
| 6,363,940 B1 | 4/2002 | Krag |
| 6,371,904 B1 | 4/2002 | Sirimanne et al. |
| 6,477,423 B1 | 11/2002 | Jenkins |
| 6,579,310 B1 | 6/2003 | Cox et al. |
| 6,626,939 B1 | 9/2003 | Burnside et al. |
| 6,638,308 B2 | 10/2003 | Corbitt, Jr. et al. |
| 6,699,205 B2 | 3/2004 | Fulton, III et al. |
| 6,725,083 B1 | 4/2004 | Burbank et al. |
| 6,730,042 B2 | 5/2004 | Fulton et al. |
| 6,746,458 B1 | 6/2004 | Cloud |
| 6,766,186 B1 | 7/2004 | Hoyns et al. |
| 6,881,226 B2 | 4/2005 | Corbitt, Jr. et al. |
| 6,893,462 B2 | 5/2005 | Buskirk et al. |
| 6,993,375 B2 | 1/2006 | Burbank et al. |
| 7,047,063 B2 | 5/2006 | Burbank et al. |
| 7,229,417 B2 | 6/2007 | Foerster et al. |
| 7,524,274 B2 | 4/2009 | Patrick et al. |
| 7,547,274 B2 | 6/2009 | Rapach et al. |
| 7,572,287 B2 | 8/2009 | Stinson |
| 7,637,948 B2 | 12/2009 | Corbitt, Jr. |
| 7,837,612 B2 | 11/2010 | Gill et al. |
| 7,871,438 B2 | 1/2011 | Corbitt, Jr. |
| 7,875,059 B2 | 1/2011 | Patterson et al. |
| 7,972,261 B2 | 7/2011 | Lamoureux et al. |
| 7,972,619 B2 | 7/2011 | Fisher |
| 8,052,658 B2 | 11/2011 | Field |
| 8,060,183 B2 | 11/2011 | Leopold et al. |
| 8,114,006 B2 | 2/2012 | Cox et al. |
| 8,157,862 B2 | 4/2012 | Corbitt, Jr. |
| 8,320,993 B2 | 11/2012 | Sirimanne et al. |
| 8,486,028 B2 | 7/2013 | Field |
| 8,600,481 B2 | 12/2013 | Sirimanne et al. |
| 8,680,498 B2 | 3/2014 | Corbitt et al. |
| 9,014,787 B2 | 4/2015 | Stubbs et al. |
| 9,199,092 B2 | 12/2015 | Stubbs et al. |
| 9,615,915 B2 | 4/2017 | Lebovic et al. |
| 9,980,809 B2 | 5/2018 | Lebovic et al. |
| 2001/0034528 A1 | 10/2001 | Foerster et al. |
| 2001/0041936 A1 | 11/2001 | Corbitt, Jr. et al. |
| 2001/0047164 A1 | 11/2001 | Teague et al. |
| 2002/0035324 A1 | 3/2002 | Sirimanne et al. |
| 2002/0072806 A1 | 6/2002 | Buskirk et al. |
| 2003/0083732 A1 | 5/2003 | Stinson |
| 2003/0195561 A1 | 10/2003 | Carley et al. |
| 2004/0109823 A1 | 6/2004 | Kaplan |
| 2004/0249457 A1 | 12/2004 | Smith et al. |
| 2005/0049489 A1 | 3/2005 | Foerster et al. |
| 2005/0074405 A1 | 4/2005 | Williams, III |
| 2005/0080338 A1 | 4/2005 | Sirimanne et al. |
| 2005/0080339 A1 | 4/2005 | Sirimanne et al. |
| 2005/0101860 A1 | 5/2005 | Patrick et al. |
| 2005/0143770 A1 | 6/2005 | Carter et al. |
| 2005/0165480 A1 | 7/2005 | Jordan et al. |
| 2005/0234336 A1 | 10/2005 | Beckman et al. |
| 2006/0025795 A1 | 2/2006 | Chesbrough et al. |
| 2006/0058570 A1 | 3/2006 | Rapach et al. |
| 2006/0116713 A1 | 6/2006 | Sepetka et al. |
| 2006/0173296 A1 | 8/2006 | Miller et al. |
| 2007/0021642 A1 | 1/2007 | Lamoureux et al. |
| 2007/0038014 A1 | 2/2007 | Cox et al. |
| 2007/0038017 A1 | 2/2007 | Chu |
| 2007/0104695 A1 | 5/2007 | Quijano et al. |
| 2007/0167665 A1 | 7/2007 | Hermann et al. |
| 2007/0167668 A1 | 7/2007 | White et al. |
| 2007/0219446 A1 | 9/2007 | Beyhan |
| 2008/0015472 A1 | 1/2008 | Ressemann et al. |
| 2008/0045773 A1 | 2/2008 | Popowski et al. |
| 2008/0082113 A1 | 4/2008 | Bishop et al. |
| 2008/0097199 A1 | 4/2008 | Mullen |
| 2008/0228164 A1 | 9/2008 | Nicoson et al. |
| 2008/0243226 A1 | 10/2008 | Fernandez et al. |
| 2008/0281388 A1 | 11/2008 | Corbitt et al. |
| 2009/0024225 A1 | 1/2009 | Stubbs |
| 2009/0030298 A1 | 1/2009 | Matthews et al. |
| 2009/0143747 A1 | 6/2009 | Dias et al. |
| 2009/0149833 A1* | 6/2009 | Cima ............... A61M 31/002 604/517 |
| 2009/0319046 A1 | 12/2009 | Krespi et al. |
| 2010/0010341 A1 | 1/2010 | Talpade et al. |
| 2010/0030072 A1 | 2/2010 | Casanova et al. |
| 2010/0042104 A1 | 2/2010 | Kota et al. |
| 2010/0222802 A1* | 9/2010 | Gillespie, Jr. ............. A61F 2/12 606/192 |
| 2011/0004094 A1 | 1/2011 | Stubbs et al. |
| 2011/0028831 A1 | 2/2011 | Kent |
| 2011/0130655 A1 | 6/2011 | Nielson et al. |
| 2011/0313288 A1 | 12/2011 | Chi Sing et al. |
| 2012/0059285 A1 | 3/2012 | Soltani et al. |
| 2012/0116215 A1 | 5/2012 | Jones et al. |
| 2012/0130489 A1 | 5/2012 | Chernomorsky et al. |
| 2013/0032962 A1 | 2/2013 | Liu et al. |
| 2013/0289389 A1 | 10/2013 | Hermann et al. |
| 2013/0289390 A1 | 10/2013 | Hermann et al. |
| 2013/0317275 A1 | 11/2013 | Stubbs |
| 2014/0100656 A1 | 4/2014 | Namnoum et al. |
| 2014/0200396 A1 | 7/2014 | Lashinski et al. |
| 2014/0275984 A1 | 9/2014 | Hermann et al. |
| 2015/0112194 A1 | 4/2015 | Stubbs |
| 2015/0250582 A1 | 9/2015 | Greenhalgh et al. |
| 2015/0313708 A1 | 11/2015 | Mayo Martin |
| 2016/0022416 A1 | 1/2016 | Felix et al. |
| 2016/0082286 A1 | 3/2016 | Stubbs et al. |
| 2016/0242899 A1 | 8/2016 | Lee et al. |
| 2017/0181842 A1 | 6/2017 | Lebovic et al. |
| 2017/0181843 A1 | 6/2017 | Lebovic et al. |
| 2017/0181845 A1 | 6/2017 | Lebovic et al. |

(56) References Cited

U.S. PATENT DOCUMENTS

| | | | |
|---|---|---|---|
| 2018/0036096 | A1 | 2/2018 | Stubbs |
| 2018/0092703 | A1 | 4/2018 | Rodriguez-Navarro et al. |
| 2018/0200020 | A1 | 7/2018 | Hermann et al. |

FOREIGN PATENT DOCUMENTS

| | | | | |
|---|---|---|---|---|
| JP | 2008143896 | A | 6/2008 | |
| JP | 2008538303 | A | 10/2008 | |
| JP | 2009500089 | A | 1/2009 | |
| JP | 2012528687 | A | 11/2012 | |
| WO | 9818408 | A1 | 5/1998 | |
| WO | 0030534 | A1 | 6/2000 | |
| WO | 2006044132 | A1 | 4/2006 | |
| WO | 2006110733 | A2 | 10/2006 | |
| WO | 2007006303 | A2 | 1/2007 | |
| WO | 2010141422 | A1 | 12/2010 | |
| WO | WO-2012122215 | A2 * | 9/2012 | ............. A61B 18/00 |
| WO | 2013009282 | A1 | 1/2013 | |
| WO | 2013163381 | A1 | 10/2013 | |
| WO | 2016014990 | A1 | 1/2016 | |

OTHER PUBLICATIONS

Extended European Search Report dated Dec. 22, 2017, for EP Application No. 15825567.9, filed on Jul. 24, 2015, 8 pages.
Extended European Search Report dated Nov. 30, 2015, for EP Application No. 13782314.2, filed on Apr. 25, 2013, 7 pages.
Extended European Search Report dated Jan. 23, 2015, for EP Application No. 10783902.9, filed on Jun. 1, 2010, 5 pages.
International Search Report dated Mar. 10, 2014 for PCT Patent Application No. PCT/US13/64168, filed on Oct. 9, 2013, 4 pages.
International Search Report dated Jul. 9, 2013, for PCT Application No. PCT/US2013/38145, Apr. 25, 2013, 2 pages.
International Search Report dated Jul. 28, 2010, for PCT Application No. PCT/US2010/036828, filed on Jun. 1, 2010, 2 pages.
International Search Report dated Oct. 28, 2015, for PCT Application No. PCT/US2015/042082, filed on Jul. 24, 2015, 2 pages.
Medical Device Daily, (Sep. 30, 2005) The Medical Technology Newspaper 9(188):pp. 1 and 9 (2 pages).
Final Office Action dated Dec. 27, 2018, for U.S. Appl. No. 15/920,126, filed Mar. 13, 2018, 18 pages.
Non-Final Office Action dated Aug. 1, 2018, for U.S. Appl. No. 14/954,589, filed Nov. 30, 2015, 16 pages.
Non-Final Office Action dated Oct. 23, 2018, for U.S. Appl. No. 13/656,068, filed Oct. 19, 2012, 22 pages.
Corrected Notice of Allowability dated Apr. 4, 2018, for U.S. Appl. No. 15/456,078, filed Mar. 10, 2017, 4 pages.
Corrected Notice of Allowability dated May 2, 2018, for U.S. Appl. No. 15/456,078, filed Mar. 10, 2017, 4 pages.
Final Office Action dated Oct. 6, 2017, for U.S. Appl. No. 15/455,977, filed Mar. 10, 2017, 14 pages.
Final Office Action dated Oct. 16, 2017, 2017, for U.S. Appl. No. 15/455,994, filed Mar. 10, 2017, 11 pages.
Final Office Action dated Oct. 20, 2017, for U.S. Appl. No. 14/954,589, filed Nov. 30, 2015, 33 pages.
Final Office Action dated Nov. 17, 2017, for U.S. Appl. No. 15/466,619, filed Mar. 22, 2017, 16 pages.
Final Office Action dated Dec. 20, 2017, for U.S. Appl. No. 13/656,068, filed Oct. 19, 2012, 16 pages.
Non-Final Office Action dated Aug. 31, 2017, for U.S. Appl. No. 15/456,078, filed Mar. 10, 2017, 8 pages.
Non-Final Office Action dated May 3, 2018, for U.S. Appl. No. 15/920,126, filed Mar. 13, 2018, 15 pages.
Notice of Allowance dated Oct. 25, 2017, for U.S. Appl. No. 15/456,078, filed Mar. 10, 2017, 5 pages.
Notice of Allowance dated Feb. 28, 2018, for U.S. Appl. No. 15/456,078, filed Mar. 10, 2017, 2 pages.
Appeal Brief (replacement) filed on Feb. 1, 2016, for U.S. Appl. No. 13/456,435, by Hermann et al., 14 pages.

Examiner's Answer to Appeal Brief mailed on Sep. 14, 2016, for U.S. Appl. No. 13/456,435, by Hermann et al., 23 pages.
Final Office Action dated Jan. 22, 2015, for U.S. Appl. No. 13/456,435, filed Apr. 26, 2012, 22 pages.
Final Office Action dated Nov. 6, 2013, for U.S. Appl. No. 13/656,068, filed Oct. 19, 2012, 14 pages.
Final Office Action dated Dec. 17, 2014, for U.S. Appl. No. 13/656,068, filed Oct. 19, 2012, 16 pages.
Final Office Action dated Mar. 21, 2016, for U.S. Appl. No. 13/802,041, filed Mar. 13, 2013, 9 pages.
Final Office Action dated Aug. 22, 2013, for U.S. Appl. No. 12/790,314, filed May 28, 2010, 24 pages.
Final Office Action dated Jun. 27, 2014, for U.S. Appl. No. 12/173,881, filed Jul. 16, 2008, 18 pages.
Final Office Action dated Oct. 11, 2016, for U.S. Appl. No. 14/808,852, filed Jul. 24, 2015, 13 pages.
Final Office Action dated May 10, 2017, for U.S. Appl. No. 13/656,068, filed Oct. 19, 2012, 18 pages.
Non-Final Office Action dated Apr. 25, 2014, for U.S. Appl. No. 13/456,435, filed Apr. 26, 2012, 17 pages.
Non-Final Office Action dated Aug. 27, 2015, for U.S. Appl. No. 13/802,041, filed Mar. 13, 2013, 9 pages.
Non-Final Office Action dated Mar. 22, 2013, for U.S. Appl. No. 13/656,068, filed Oct. 19, 2012, 17 pages.
Non-Final Office Action dated Apr. 3, 2014, for U.S. Appl. No. 13/656,068, filed Oct. 19, 2012, 12 pages.
Non-Final Office Action dated Dec. 1, 2015, for U.S. Appl. No. 13/656,068, filed Oct. 19, 2012, 23 pages.
Non-Final Office Action dated Jan. 3, 2013, for U.S. Appl. No. 12/790,314, filed May 28, 2010, 11 pages.
Non-Final Office Action dated Oct. 10, 2014, for U.S. Appl. No. 12/790,314, filed May 28, 2010, 7 pages.
Non-Final Office Action dated May 8, 2015, for U.S. Appl. No. 14/581,146, filed Dec. 23, 2014, 10 pages.
Non-Final Office Action dated May 5, 2017, for U.S. Appl. No. 15/455,994, filed Mar. 10, 2017, 11 pages.
Non-Final Office Action dated Aug. 16, 2011, for U.S. Appl. No. 12/173,881, filed Jul. 16, 2008, 12 pages.
Non-Final Office Action dated Sep. 23, 2016, for U.S. Appl. No. 14/581,807, filed Dec. 23, 2014, 16 pages.
Non-Final Office Action dated Mar. 25, 2016, for U.S. Appl. No. 14/808,852, filed Jul. 24, 2015, 11 pages.
Non-Final Office Action dated Jun. 29, 2016, for U.S. Appl. No. 14/808,852, filed Jul. 24, 2015, 14 pages.
Non-Final Office Action dated Jan. 5, 2017, for U.S. Appl. No. 14/954,589, filed Nov. 30, 2015, 12 pages.
Supplemental Notice of Allowability dated Mar. 10, 2017, for U.S. Appl. No. 14/808,852, filed Jul. 24, 2015, 2 pages.
Non-Final Office Action dated Apr. 21, 2017, for U.S. Appl. No. 15/456,078, filed Mar. 10, 2017, 10 pages.
Non-Final Office Action dated May 24, 2017, for U.S. Appl. No. 15/455,977, filed Mar. 10, 2017, 13 pages.
Notice of Allowance dated Sep. 25, 2015, for U.S. Appl. No. 14/581,146, filed Dec. 23, 2014, 9 pages.
Notice of Allowance dated Mar. 17, 2015, for U.S. Appl. No. 12/790,314, filed May 28, 2010, 8 pages.
Notice of Allowance dated Feb. 1, 2017, for U.S. Appl. No. 14/808,852, filed Jul. 24, 2015, 7 pages.
Reply Brief filed on Nov. 14, 2016, for U.S. Appl. No. 13/456,435, by Hermann et al., 5 pages.
Written Opinion of the International Searching Authority dated Jul. 9, 2013, for PCT Application No. PCT/US2013/38145, Apr. 25, 2013, 6 pages.
Written Opinion dated Mar. 10, 2014 for PCT Patent Application No. PCT/US13/64168, filed on Oct. 9, 2013, 6 pages.
Written Opinion of the International Searching Authority dated Jul. 28, 2010, for PCT Application No. PCT/US2010/036828, filed on Jun. 1, 2010, 6 pages.
Written Opinion of the International Searching Authority dated Oct. 28, 2015, for PCT Application No. PCT/US2015/042082, filed on Jul. 24, 2015, 4 pages.
Lakeshore Biomaterials, "General Mechanical Properties Chart". Feb. 19, 2009, 1 page.

(56) References Cited

OTHER PUBLICATIONS

Middleton, J., "Tailoring of Poly(lactide-co-glycolide) to Control Properties", Lakeshore Biomaterials, 2007, 67 pages.
Authorunknown, "PURASORB® Technology", PURAC Biomaterials, 2009, 1 page.

* cited by examiner

IMPLANTABLE DEVICES AND TECHNIQUES FOR ONCOPLASTIC SURGERY

CROSS-REFERENCE TO RELATED APPLICATION

This application is a continuation of pending U.S. patent application Ser. No. 15/456,030, filed Mar. 10, 2017, which is a continuation of U.S. patent application Ser. No. 14/808,852, filed Jul. 24, 2015, now issued U.S. Pat. No. 9,615,915, which claims priority to U.S. Provisional Application Ser. No. 62/029,358, filed Jul. 25, 2014, which are hereby incorporated by reference in their entirety.

FIELD OF INVENTION

Described herein are devices for placement in surgically created soft tissue spaces, potential spaces, or cavities. The implantable devices generally include a bioabsorbable body having an open framework that facilitates attachment of tissue thereto, while supporting adjacent margins of the surgical resection cavity in a manner that helps avoid post-surgical deformities. Methods for using the implantable devices in oncoplastic surgery are further described.

BACKGROUND

The treatment and/or prevention of breast cancer typically includes surgery to remove an area of tissue believed or proven to be cancerous or at high risk for developing cancer over time. Various surgical procedures are used to remove tissue of this nature, but in general, at least a section of the breast is removed to prevent further growth of abnormal tissue. Such surgical procedures include removal of a portion of the breast (partial mastectomy), or if needed, the entire breast is removed (mastectomy). Surgery is often followed by additional treatments to prevent recurrence of the cancer, and these treatments may include radiation therapy and/or chemotherapy. Soon after surgery is performed, bodily fluids known as seroma fluid usually fill the surgical cavity. This fluid contains varying amounts of bloody and proteinaceous materials, cells that help the body during the healing process, as well as anti-inflammatory biological elements. Seroma fluid almost immediately fills the surgical cavity and may temporarily appear to restore the shape of the breast. However over time, the body absorbs the seroma fluid, resulting in the cavity collapsing on itself to varying degrees. In many cases, scar tissue develops and can cause adherence of the margins or walls of the cavity as a natural part of the healing process. This process can result in undesirable deformities of the breast, ranging from dimpling of the overlying skin to large divots and concavities that are unsightly and painful. In addition, radiation of the area compounds these effects and makes correction of these painful abnormalities very challenging to address. When a mastectomy is performed, inadequate amounts of skin and tissue may remain to effectively reconstruct the breast to an acceptable aesthetic appearance.

Recent advances in breast cancer treatment combine the philosophy and/or principles of aesthetic and reconstructive surgery (plastic surgery) with the principles and techniques of surgical oncology in an attempt to restore the form and/or function of the breast at the time of (or after) removal of abnormal tissue. This relatively new field of surgery, referred to as oncoplastic surgery, generally involves removing cancerous tissue and then manipulating and utilizing various body tissues or rearranging the adjacent remaining tissue to help correct any defects or gaps that were created by the surgery. In this manner adjacent tissues are used to fill the voids left in surgery, which can decrease seroma formation and improve the ultimate outcome, particularly in regards to shape and contour of the breast. For example, tissue flaps may be created to provide easier manipulation, approximation, rotation and closure of tissues in and around the surgical wound. There may be situations, however, when insufficient tissue is present to create these flaps in the size needed, or to create a flap at all resulting in a smaller or malformed (deformed) breast after surgery. In other instances, the flap may be created in such a way that its blood supply is compromised, ultimately causing the flap and surrounding tissues to die, leading to fat necrosis and other undesirable patient outcomes. Accordingly, it would be desirable, for example, to have a device and/or technique to employ in circumstances where wound tension and sparsity of tissue may otherwise cause a long-standing deformity such as following removal of a portion of the breast. An important goal of the devices and approaches described herein is to improve surgical techniques for breast surgery.

SUMMARY

Described herein are methods of breast surgery and devices for use thereof. The methods and devices may be useful in oncoplastic surgery, where it is desirable to preserve and/or improve the shape, size, and contour of an area of the body where tissue has been surgically removed, such as the breast. In some aspects, the methods and devices provide support for the tissue and may help to reapproximate tissues after surgery to prevent deformity of the skin overlying the cavity. For example, the methods and devices may be beneficial when insufficient tissue is present to create a tissue flap, or in the instance where sufficient tissue is present to form a tissue flap but its creation would compromise the blood supply to the tissue, causing tissue death and ultimately fat necrosis.

The methods of breast surgery described herein generally include the steps of removing tissue (such as breast tissue) to create a cavity or void (where the cavity or void may disrupt and/or deform the shape, size, or contour of the breast); placing an oncoplastic surgery device into the cavity, where the oncoplastic device comprises a body having an open framework formed primarily of a supportive bioabsorbable material having anterior, posterior, and lateral regions; manipulating, or otherwise mobilizing, undermining, and/or rotating adjacent tissues surrounding the cavity; and at some time during the surgical procedure, attaching the open framework to the surrounding tissue, typically via monofilament absorbable suture. This approach eliminates the need for the device to fill the defect, cavity or void with foreign material, as is described in, for example, U.S. Pat. No. 7,637,498 to Corbitt, Jr ("Corbitt"). In contrast to the approach described by Corbitt, the approaches described herein include using a patient's native tissue in combination with a bioabsorbable open framework device to help reconstruct the cosmetic deformity caused by the surgical tissue resection.

Alternatively, the methods of breast surgery may include removing an area of breast tissue to create a cavity, an opening, or a space; placing an oncoplastic device into the cavity, the opening, or the space, the oncoplastic device comprising a body having an open framework and formed of a bioabsorbable material, the open framework comprising an anterior, a posterior, and lateral regions, and an array of cross-member elements that impart an ellipsoid profile to the open framework; manipulating tissue surrounding the cavity, the opening, or the space; and attaching the open framework to the manipulated tissue.

The oncoplastic devices described herein are implantable and may include a body formed of a bioabsorbable material. The body is generally configured to have an open framework so that it can be attached to tissues surrounding the cavity, e.g., by passing suture around or through the open framework and also through the adjacent tissue. The body has a length, width, and height, and may be comprised of one or more framework elements. In some variations, the body has a geometric profile that is generally of the form of a tri-axial ellipsoid or an oblate ellipsoid of revolution. The framework typically has sufficient rigidity to be sutured to adjacent tissue without significantly deforming the shape of the framework element. It also may be useful for the framework elements to have a degree of compliance, or "give" whereby the device elements are able to move while in position to accommodate patient movement. The compliant nature of the device framework, combined with the open architecture of the framework may allow the surrounding tissues to be integral within the body of the device, and may create a feeling of resilience or compliance when the area of the body overlying the device is touched or pressed upon through the skin, giving the device a natural feel to the patient. This compliance in the framework elements may also serve as a "strain relief" to the tissue that is sutured to the device, to minimize disruption of the suture/tissue interface. In some variations, it may be beneficial for the implantable oncoplastic devices to include a body formed of a bioabsorbable material and having an open framework, wherein the body has a length, width, and height, and wherein the open framework comprises a periphery and an array of cross-member elements that impart an ellipsoid profile to the open framework.

Additionally, the oncoplastic devices disclosed herein are generally structured in a way that helps to support the tissue during healing, while allowing body fluids, e.g., seroma fluid, to flow freely within them. The seroma fluid can organize within the oncoplastic device and heal in a manner that reconstitutes the form, shape, size and or contour of the breast. This process of regrowth generally mimics the ability of the breast to fill in the defect as seen with autologous fat grafting. Accordingly, due to their structure, the devices generally provide a means of autologous fat grafting without having to harvest and process fat from a remote surgical site. This in turn allows the breast to heal in a more natural manner and avoid potential mammographic artifacts such as calcifications associated with fat necrosis (unsuccessful fat grafting). As a result of the breast tissue being able to heal in a less stressful manner, the mammographic results may provide a more acceptable method for following the tumor resection area for recurrence of cancer.

The oncoplastic devices may further include a plurality of discrete radiographically visible elements, e.g., marker elements or marker clips, to aid in visualization of the device as it was placed at the site of the surgical resection cavity and sutured to the tissues at greatest risk for cancer recurrence. Given the specific arrangement of the spacing of these radiographically visible elements, they define the area to which the radiologist or other clinicians may direct their attention when they are seen using clinical imaging techniques such as mammography, CT, etc. Treatments after surgery often include radiation, and these visible elements of the device may be useful in a variety of clinical circumstances, such as when focusing external radiation to target tissue surrounding the cavity if radiation therapy is subsequently employed.

Additionally or alternatively, the framework of the oncoplastic device may be composed of a bioabsorbable element that has a relatively tissue-equivalent z-number that allows it to be relatively radiolucent on some types of imaging such as mammography, while marker clip components coupled thereto are radiopaque and easily seen on many forms of clinical imaging (e.g., CT, MR, kV X-ray).

DETAILED DESCRIPTION

Figure 1:
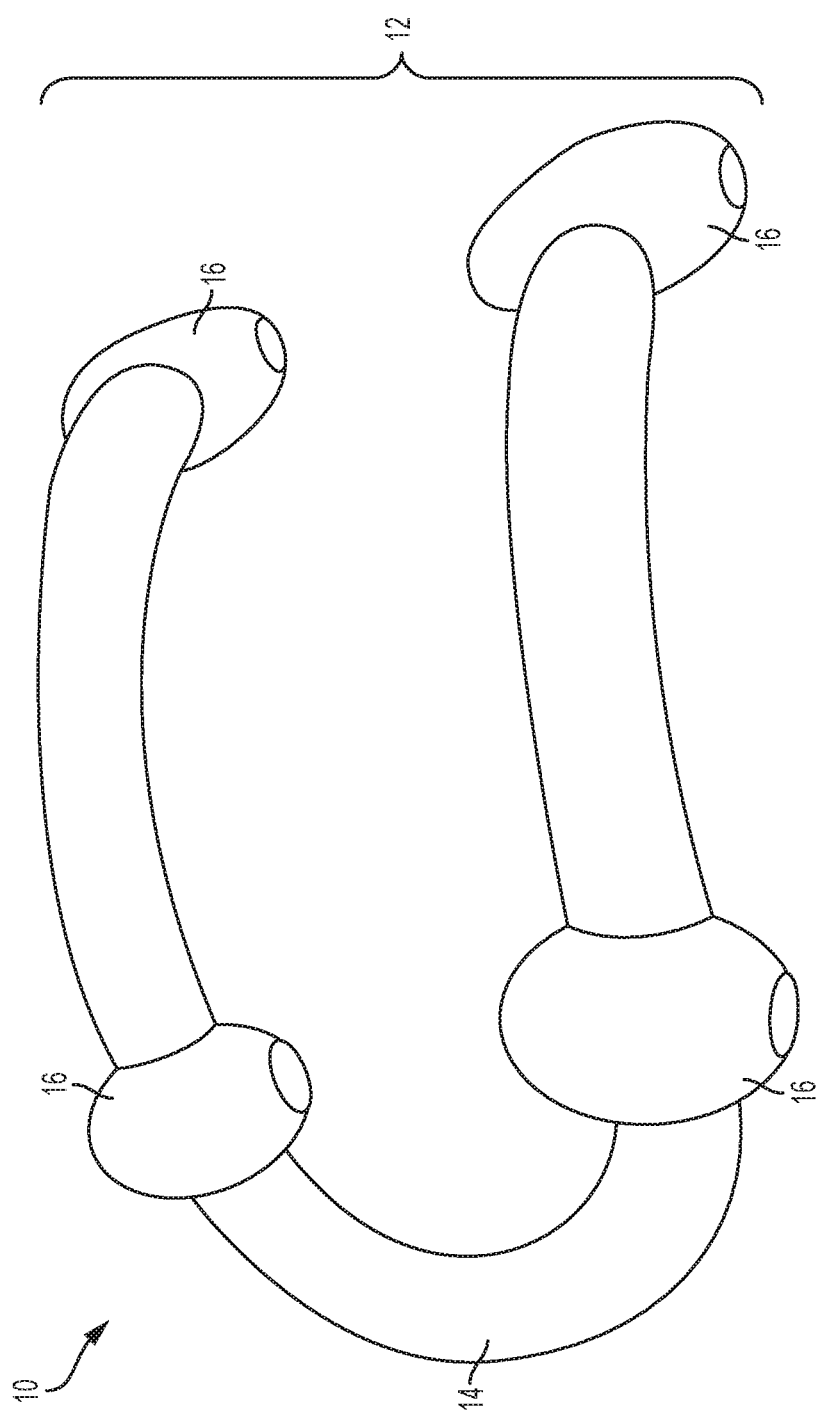
FIG. 1 shows one variation of an oncoplastic device comprising a single, U-shaped framework element.

Described herein are methods of breast surgery and devices for use thereof. As previously mentioned, the methods and devices may be useful in oncoplastic surgery, where it may be desirable to preserve and/or improve the size, shape, and/or contour of the breast. More specifically, the methods and devices may facilitate the reapproximation of tissues in a manner that provides for an improved surgical outcome, which may lead to decreasing fibrosis, pain, and scar tissue formation, and may also contribute to an improved aesthetic/cosmetic outcome, as well as mammographic outcome.

Oncoplastic Devices

The devices described herein are implantable oncoplastic surgical devices/tools/implants (also referred to herein as "oncoplastic devices" or "devices") that may comprise a three-dimensional body having a length, width, and height.

The body may have an open framework or trellis-like framework that is formed from one or more framework elements. The devices are generally configured for open surgical placement into a surgical area where tissue has been removed, e.g., lumpectomy, partial mastectomy, mastopexy, and reduction mastopexy, and employed in a way that is useful in avoiding post-surgical deformities of an anatomic region.

In some variations, the device is placed and secured with suture during the same operation (and through the same surgical incision) as the surgical removal of the tissue (e.g., the device is placed and secured during the lumpectomy procedure). When placed at the original time of surgery, the open framework and external elements on the body of the device may allow for the dermal lymphatics and vasculature of the breast to heal more appropriately. However, in certain circumstances, the device may be used for partial breast reconstruction in patients that have had previous breast surgery with poor cosmetic results such as a concavity or distortion of the breast. In these circumstances, the device is used to fill some of the void left by removal of a given volume of breast tissue, as well as restore the contour and shape of the breast. The semi-rigid, but pliable framework may allow for the device to "plump up" a previously depressed area of the breast, and may provide a mechanism for autologous fat grafting to occur spontaneously by the body itself without having to harvest, process and transfer fat into the area. Scar tissue may be sutured to the framework of the device, thereby decreasing the skin tension on the overlying wound.

In some variations, the devices are secured to tissues that have been mobilized from areas adjacent to the tissue cavity, e.g., tissue flaps. In instances where mobilization of tissue is not necessary, the device may be implanted with or without being secured to tissue of the cavity, and the cavity is closed around and/or through the device. The devices described herein can be used by surgeons who do not actively reapproximate the opposing walls of a tissue cavity created by, e.g., partial mastectomy/lumpectomy. In addition, the devices can be used by surgeons who choose to surgically reapproximate at least a portion of the breast tissue surrounding the lumpectomy cavity. This reapproximation, sometimes called cavity closure, is typically accomplished by suturing the breast tissue on either side of the lumpectomy cavity and drawing the tissue together prior to skin closure. In addition to the devices disclosed here, other suitable devices, e.g., those structures disclosed in commonly owned U.S. application Ser. No. 13/456,435 may be used with the surgical methods further described below.

The framework material of the device may be relatively rigid (or non-compressible), but the overall device can be compliant and pliable or deformable under modest loads encountered while implanted. In general, the open framework is configured to be rigid enough to support the surrounding tissue without fully collapsing, yet have large enough openings within it to allow substantial volumes of tissue to be pulled over or under it, be wrapped around it in various directions, or to flow through the open framework. The open architecture of the oncoplastic devices is generally intended to maximize the opportunity for tissue ingrowth, tissue mobilization, tissue approximation and/or fluid communication across the peripheral boundary of the device. The open architecture may also allow for the passage of suture around a portion of the device at multiple locations of the device by the clinician to help secure the device to adjacent tissue. There may also be specific sites along the device's structure intended for a more precise placement of suture or other fastening mechanisms in order to secure the device in a specific or particular manner, orientation or position.

In addition, those configurations of the device which are more linear or planar (i.e., having a length and/or width greater than its height, and in some instances having a contoured edge to the device) may be employed to improve size, shape, and/or contour of the breast. For example, the contoured edge can be incorporated into the tissues of the breast so as to impart a contour or projection to the reconstructed area of the breast thereby adding contour to the skin surface of the breast for improved cosmetic outcomes. This maneuver can be performed, for example, by placing the device in the center of the breast during a central lumpectomy to provide additional projection. Alternatively, the device may be placed in an outwardly projecting orientation (perpendicular to the skin surface), for example, underneath a vertical incision used for reduction mammoplasty. The devices may also be used with or without radiographically visible elements in these circumstances and can provide a visual cue for the radiologist and radiation oncologist for post-op treatment or long term follow up of the surgical area.

In some variations, the body of the oncoplastic device is formed of a bioabsorbable material, e.g., a bioabsorbable polymer, so as to not leave behind a permanent implant that would interfere with long term clinical imaging during patient follow-up or overall patient acceptance. Exemplary bioabsorbable polymers include without limitation, collagen, polygalactin, poliglecaprone, polylactic acid, polyglycolic acid, caprolactone, lactide, glycolide, and copolymers and blends thereof. The bioabsorbable structure may function as a trellis, support, bridge, etc., for tissues to be sutured to, and with openings to allow tissue to flow or be pulled through it. Further, the structure may allow the tissue to heal while being supported by the underlying device, as well as help to decrease the amount of tension on different aspects of the surgical wound, and/or surrounding and overlying tissues such as fat, muscle, breast tissue, or skin.

The open framework of the oncoplastic devices generally comprises one or more framework elements. The framework elements may be shaped or constructed to at least partially conform to the contours of the tissue cavity while also preventing collapse of the cavity if desired to maintain and/or improve the shape, size and/or contour of the specific area of the body, such as the breast. Maintaining separation of cavity tissues is believed to be important because the adherence of tissues during the healing process may exacerbate the scarring process and/or lead to severe fibrotic changes causing painful and unsightly aesthetic/cosmetic deformities as well as scar tissue that can obscure breast tissue during post-op follow-up (e.g., mammography).

In one variation, the oncoplastic devices include a single (unitary), continuous, framework element. The single framework element may be curved, arcuate, U-shaped, spiral-shaped, undulating, circular, ovoid, flattened (sheet like) or combinations of the foregoing, etc. In another variation, the oncoplastic devices include a plurality of framework elements. The framework elements may be characterized as base elements and spacer elements. The framework elements may take the general geometric profile shape of an ellipsoid or otherwise be configured to impart an ellipsoid geometric shape to the oncoplastic device. The base elements may take the form of a circle or an oval, to which is attached one or more spacer elements that provide height to the device (and thus separation of cavity tissues).

The circular and ovular base elements may have any diameter suitable for the intended area of implantation. In some variations, the diameter of the circular base element may range from about 2.0 cm to about 5.0 cm. For example, the diameter of the circular base may be about 2.0 cm, about 2.5 cm, about 3.0 cm, about 3.5 cm, about 4.0 cm, about 4.5 cm, or about 5.0 cm. There may be instances where the circular base diameter is less than 2.0 cm or more than 5.0 cm. Similarly, the diameters (short and long diameters) of the ovular base element may range from about 2.0 cm to about 6.0 cm. For example, the ovular base diameters (short and long diameters) may be about 2.0 cm, about 2.5 cm, about 3.0 cm, about 3.5 cm, about 4.0 cm, about 4.5 cm, about 5.0 cm, about 5.5 cm, or about 6.0 cm. Any suitable combination of short and long diameters may be employed for the ovular base element. It is also understood that other framework element shapes and geometries may be used.

The length, width, and height of the oncoplastic devices may be the same or different. In some variations, the devices are configured to have one dimension that is substantially less than the other two dimensions. For example, the height of the devices may be substantially less than their width and length. It may be beneficial to use such low profile devices in shallow tissue cavities or areas where there is minimal overlying tissue, small cavities, or where there is no cavity, as in e.g., reduction mastopexy. The height of the devices may range from about 0.2 cm to about 4.0 cm. For example, the height of the device may be about 0.2 cm, about 1.0 cm, about 1.5 cm, about 2.0 cm, about 2.5 cm, about 3.0 cm, about 3.5 cm, or about 4.0 cm. The width and length may range from about 1.0 cm to about 4.0 cm. For example, the width and length may be about 1.0 cm, about 1.5 cm, about 2.0 cm, about 2.5 cm, about 3.0 cm, about 3.5 cm, or about 4.0 cm. In one variation, the device height is about 1.0 cm, width is about 2.0 cm, and the length is about 3.0 cm. It is understood that the dimensions of the device can be modified or adjusted to suit the area of intended use.

The open framework may also include a plurality of discrete radiographically visible elements spaced thereon, or therapeutic drugs, radioactive implant seeds, etc., for potential treatment of cancer or it may contain various elements to improve or expedite tissue healing and/or prevent infection such as growth factors, vitamins, hemostatic agents, antibacterial agents, etc. These elements can be attached to the framework in a variety of ways. The elements may also be symmetrically or asymmetrically spaced upon the framework. The discrete radiographically visible elements generally assist in delineating a three-dimensional region or volume of tissue for subsequent clinical imaging for radiation therapy planning and delivery, and long term follow-up. They may also provide a visual cue for the targeting and alignment of proper patient positioning during radiation treatments, e.g., serving as a fiducial marker, and provide a mechanism for clinicians to accurately target an area that may move between or during radiation treatments. This may allow for greater accuracy in positioning from day to day during different sessions of radiation treatment. The device is generally intended to be placed into an open surgical resection cavity, typically at the site of tumor/cancer excision. Similarly the device allows for tracking the surgical site for the possibility of a delayed recurrence of cancer, and having a fixed plurality of indicators allows the clinicians (e.g., the radiologist reading mammograms) to draw their attention to the exact surgical site, which is typically the most common place for recurrence to occur over time.

Figure 2:
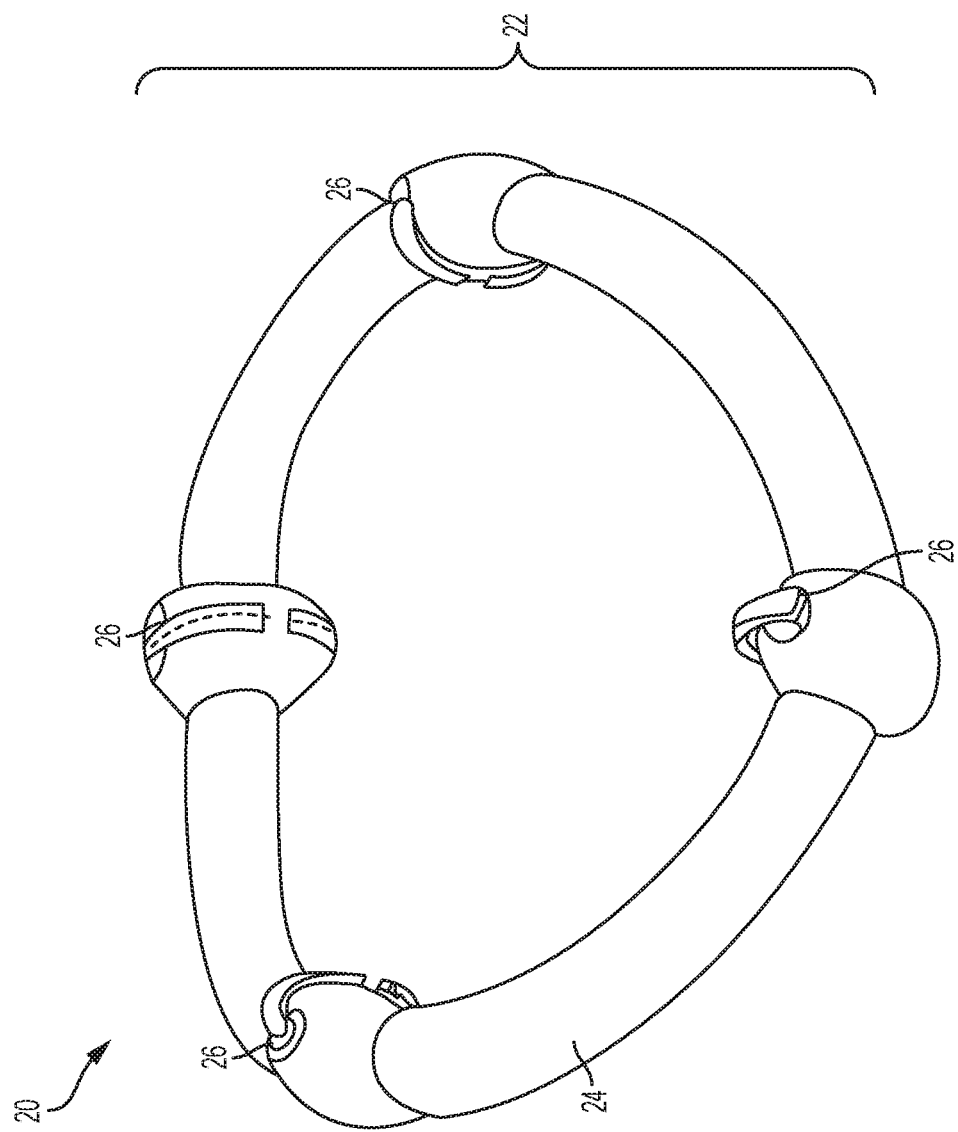
FIG. 2 shows another variation of an oncoplastic device comprising a single, circular framework element.
Figure 3:
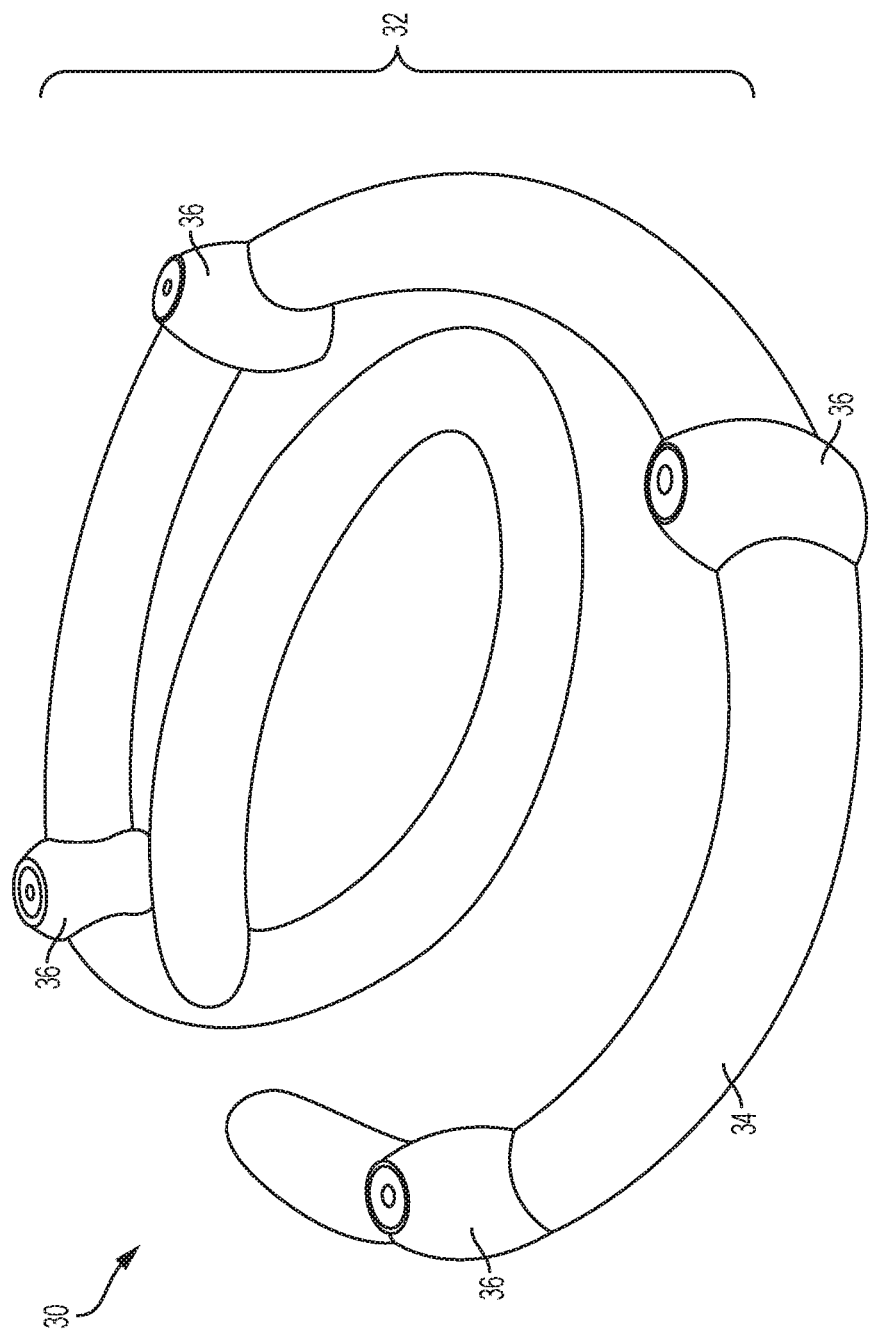
FIG. 3 shows another variation of an oncoplastic device comprising a single, spiral-shaped framework element.

FIG. 1 depicts one variation of an oncoplastic device. The oncoplastic device (10) has an open framework body (12) that includes a single, U-shaped framework element (14). A plurality of radiographically visible elements (not shown) may be provided in structures (16) that are spaced upon the framework element (12). The framework element (14) may be slightly undulated so that upon placement within a tissue cavity, the marker elements may be positioned to prescribe a 3 dimensional (3D) volume. In another variation, as shown in FIG. 2, the oncoplastic device (20) includes an open framework body (22) comprising a single, continuous circular framework element (24) having a plurality of radiographically visible elements (26) spaced thereon. In yet a further variation, as shown in FIG. 3, the oncoplastic device (30) includes an open framework body (32) comprising a single, spiral-shaped framework element (34). A plurality of radiographically visible elements (not shown) may be provided in structures (36) that are spaced upon the framework element (34).

Figure 4:
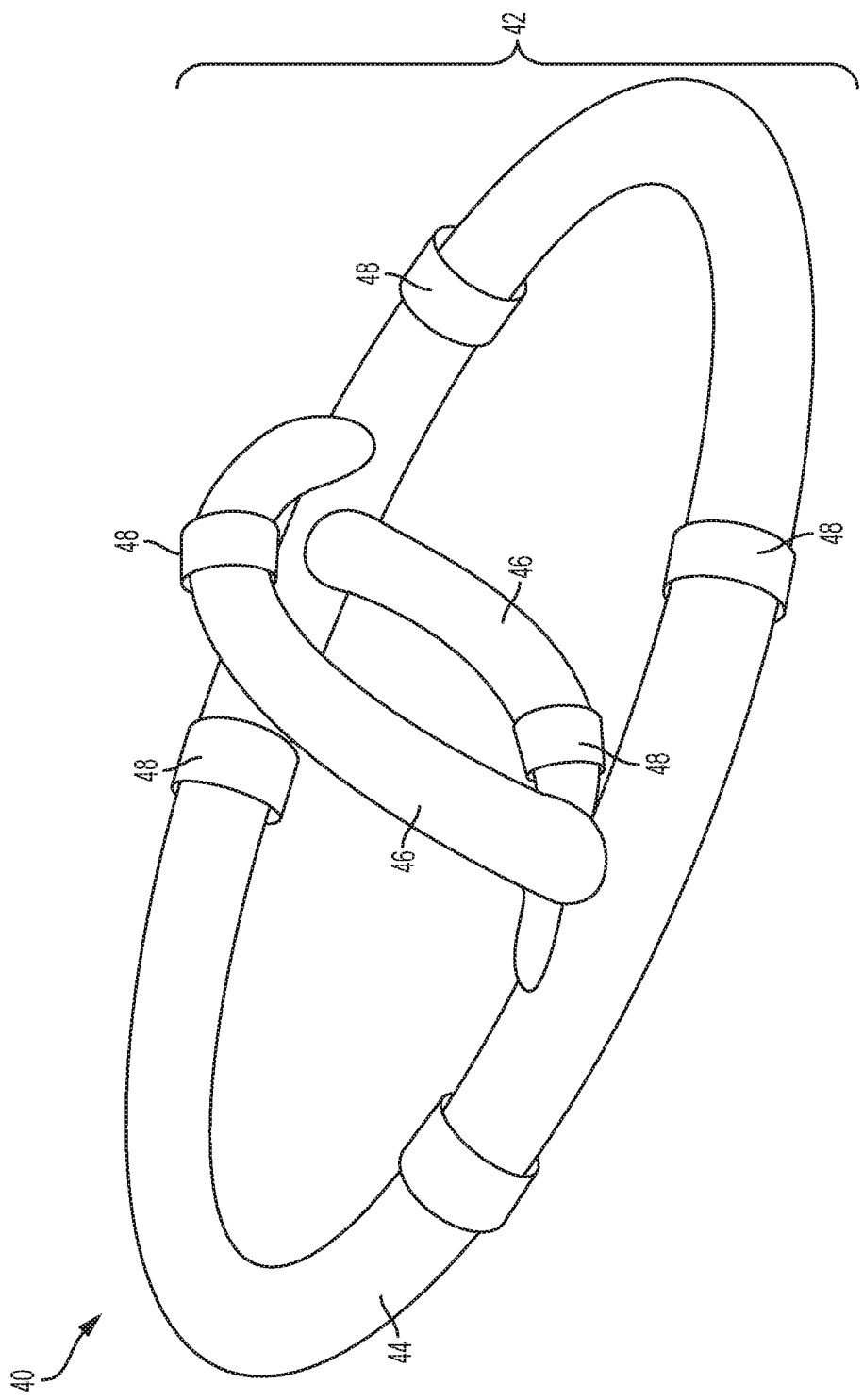
FIG. 4 shows another variation of an oncoplastic device comprising a plurality of framework elements.

FIGS. 4-8 depict variations of oncoplastic devices that include a plurality of framework elements. Referring to FIG. 4, oncoplastic device (40) has an open framework body (42) that includes a circular base element (44) and two curved or arcuate spacer elements (46). As shown in the figure, the ends of the spacer elements (46) are fixed to the base element (44). Further, the curved or arcuate spacer elements (46) are offset from one another in the longitudinal plane. It may be easier to manufacture (e.g., by molding) an oncoplastic device having this configuration. Again, a plurality of radiographically visible elements such as elements (48) may be spaced upon the framework elements effectively at the extremities of the x, y, and z axes of the device (as shown) or along other portions of the framework elements.

Figure 5:
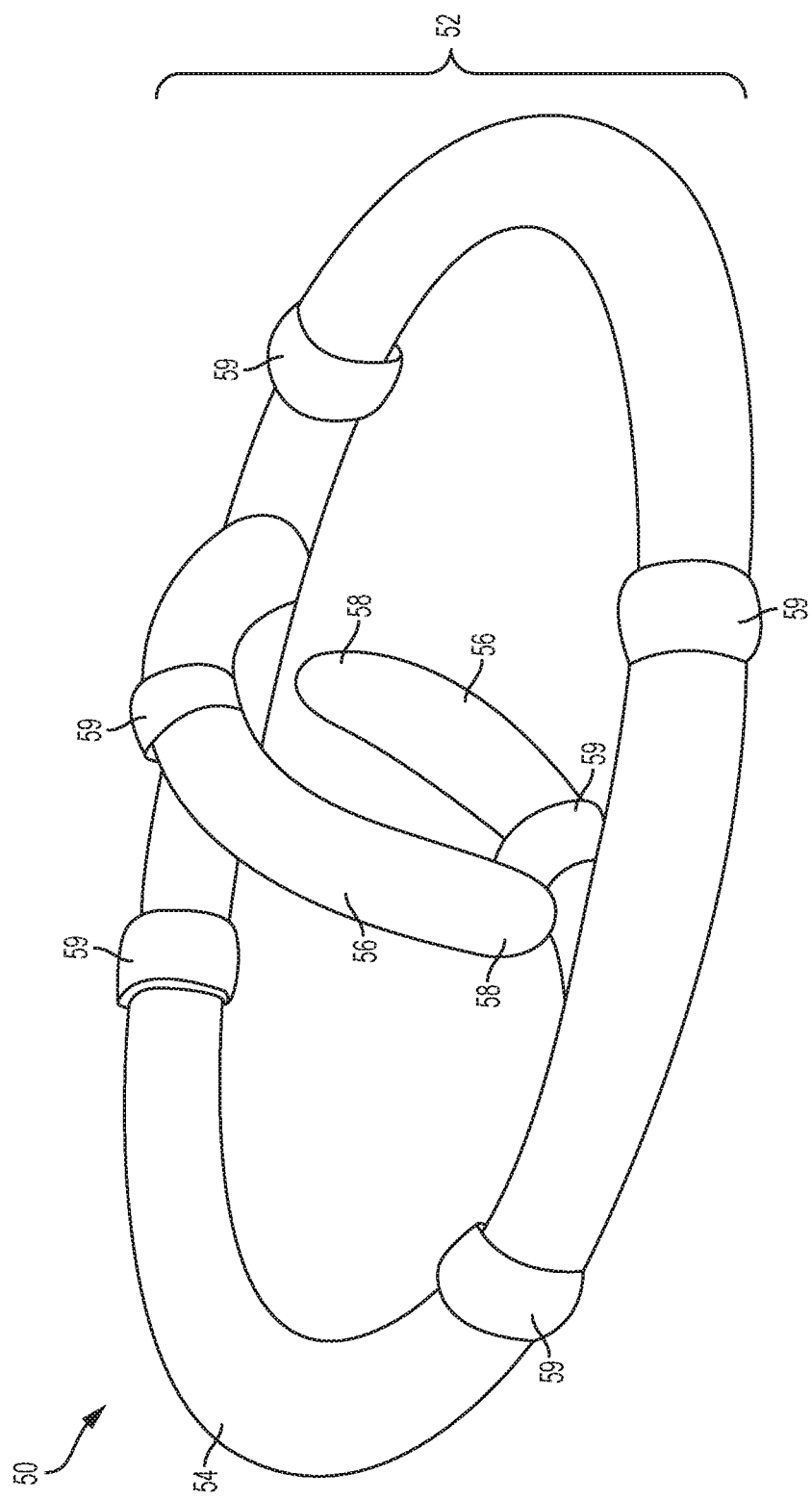
FIG. 5 shows another variation of an oncoplastic device comprising a plurality of framework elements configured to impart compressibility to the device.

FIG. 5 depicts another variation of an oncoplastic device including a plurality of framework elements. Referring to FIG. 5, oncoplastic device (50) has an open framework body (52) including an ovoid base element (54) and two curved or arcuate spacer elements (56). In this variation, one end (58) of the spacer elements (56) is not attached to the base element (54) to impart some compliance or compressibility to the overall device. A plurality of radiographically visible elements (59) (e.g., titanium, pyrolytic carbon, gold, or other radiopaque biocompatible substance) are also spaced upon and/or embedded within the framework elements, at desired locations as described elsewhere herein.

Figure 6:
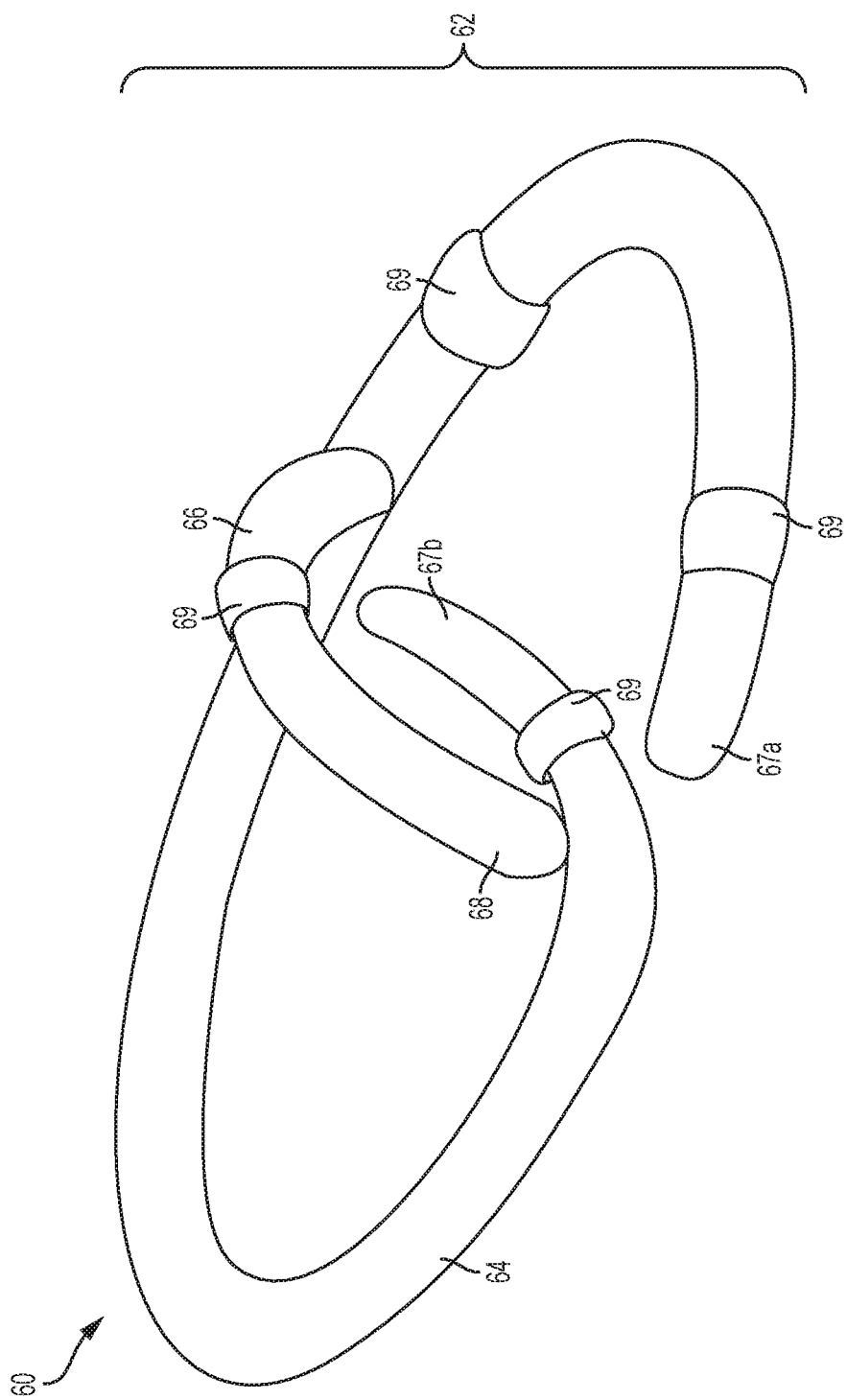
FIG. 6 shows another variation of an oncoplastic device comprising a plurality of framework elements configured to impart compressibility to the device.

FIG. 6 depicts yet another variation of an oncoplastic device including a plurality of framework elements. In FIG. 6, oncoplastic device (60) includes an open framework body (62) comprised of circular base element (64) and a single curved or arcuate spacer element (66). In this variation, the ends (67a, 67b) of the base element (64) are separated, and one end (67b) curved outward in the direction away from the opposing spacer element (66). The end (68) of spacer element (66) and end (67b) of base element (64) are shown as attached to other areas of the base element (64), but they need not be attached, e.g., if increased compressibility and or torsional deflection of the base element (64) is desired. A plurality of radiographically visible elements (69) are also spaced along the framework elements.

Figure 7:
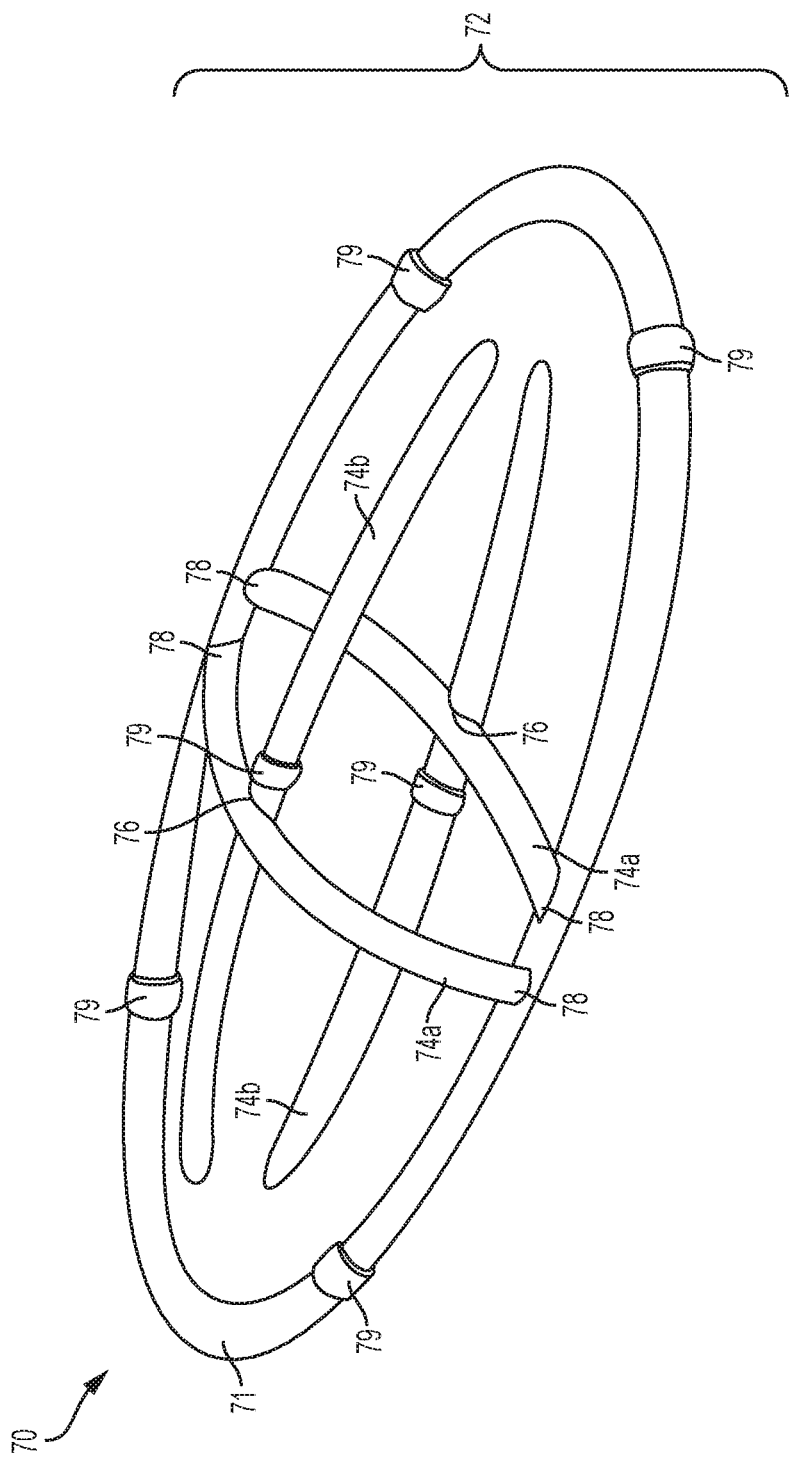
FIG. 7 shows another variation of an oncoplastic device comprising a plurality of framework elements.

A further variation of an oncoplastic device comprising a plurality of framework elements is shown in FIG. 7. Referring to the figure, oncoplastic device (70) includes an open framework body (72) having an ovoid base element (71) and two pairs of spacer elements (74a and 74b) (for a total of four) with each pair residing in orthogonal planes. Spacer elements (74b) are attached to the other pair of spacer elements (74a) at fixation points (76). The ends (78) of spacer elements (74a) are attached to base element (71). A plurality of radiographically visible elements (79) are also spaced along the framework elements.

Figure 8:
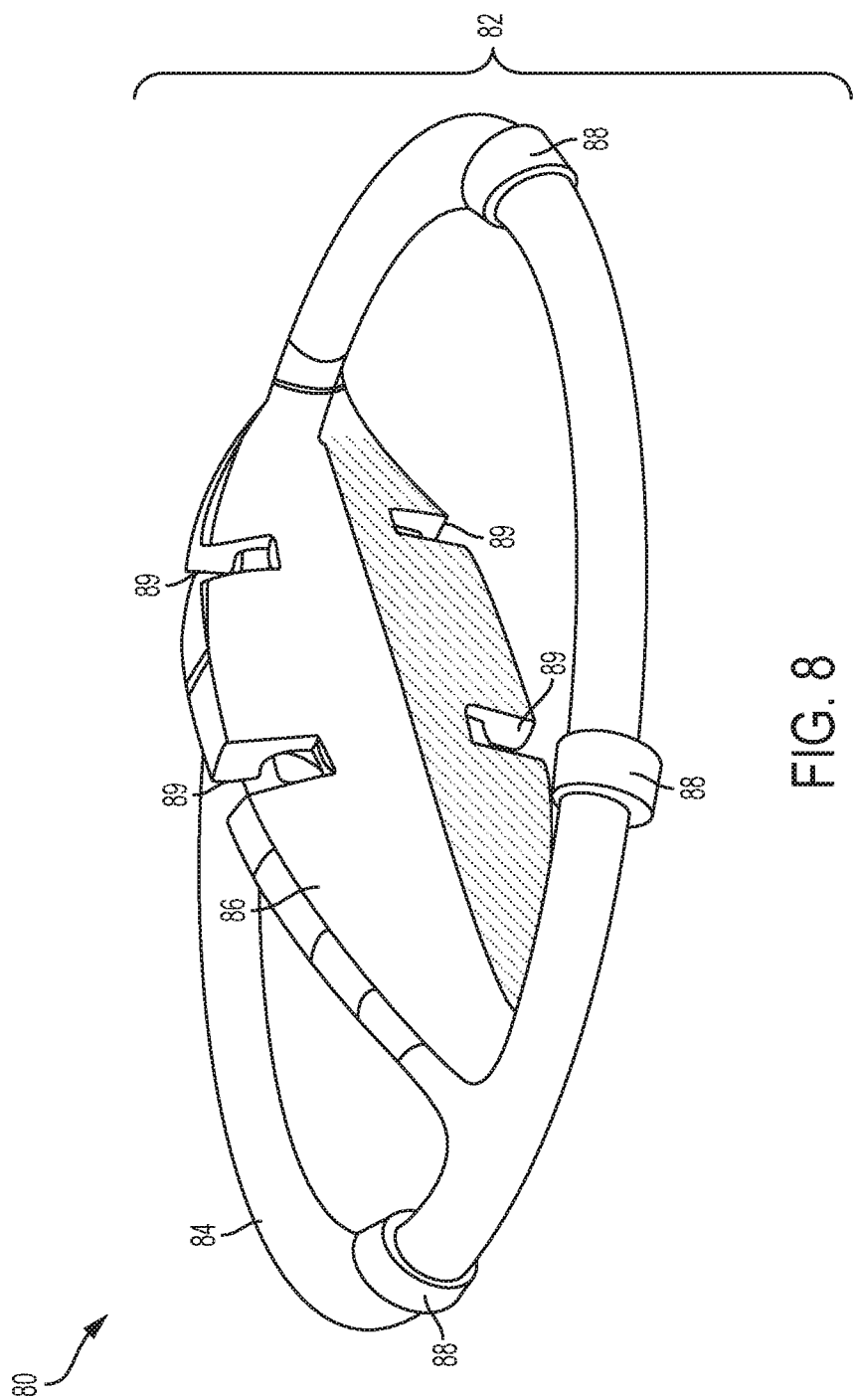
FIG. 8 shows another variation of an oncoplastic device comprising a plurality of framework elements, where one of the framework elements consists of a circular base and another framework element spans the diameter of the circular base.

Alternatively, the oncoplastic device may be configured as shown in FIG. 8. In FIG. 8, oncoplastic device (80) comprises an open framework body (82) formed by a plurality of framework elements, circular base element (84) and a solid, planar, spacer element (86), which is attached to the base element (84). It may be easier to manufacture (e.g., by molding) an oncoplastic device having this configuration. Again, a plurality of radiographically visible elements such as elements (88) may be spaced upon the framework elements. Cutouts (89) in the solid, planar, spacer element may also be provided to hold radiographically visible elements.

Figure 11:
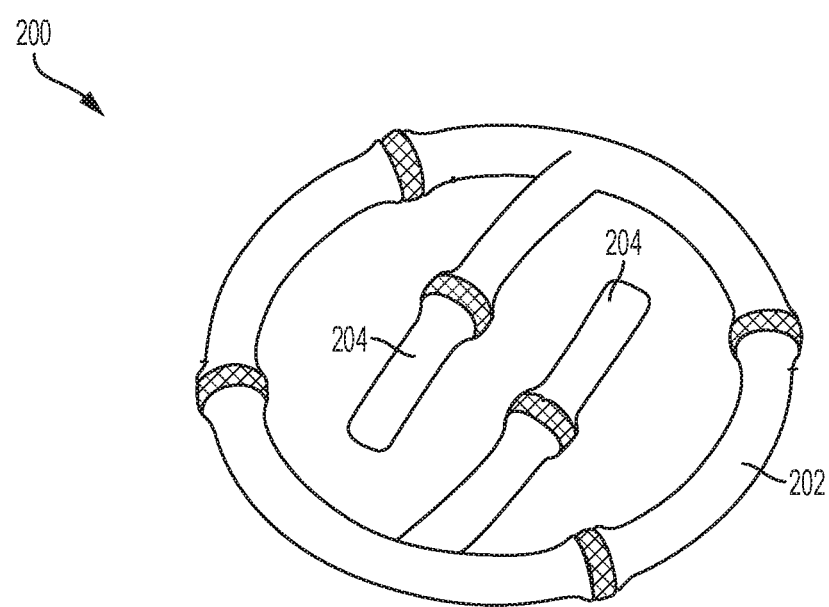
FIGS. 11-13 show perspective views of other variations of an oncoplastic device comprising a plurality of framework elements, where the framework elements include a circular base (FIG. 11), an oval base (FIGS. 12A-12C), and cross-member elements of varying heights (FIG. 13).
Figure 12A:
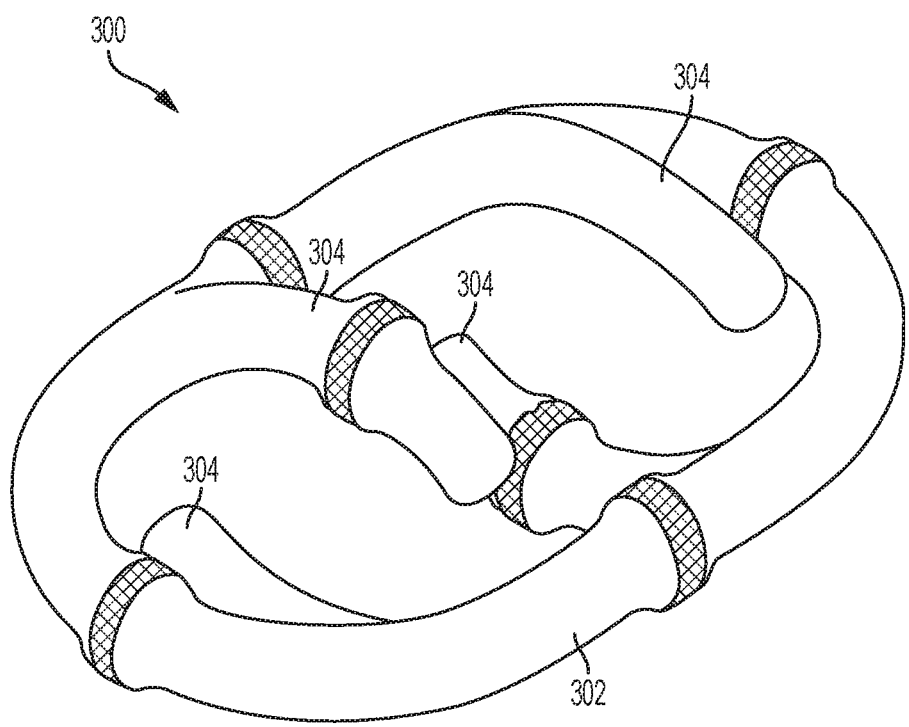
Figure 12B:
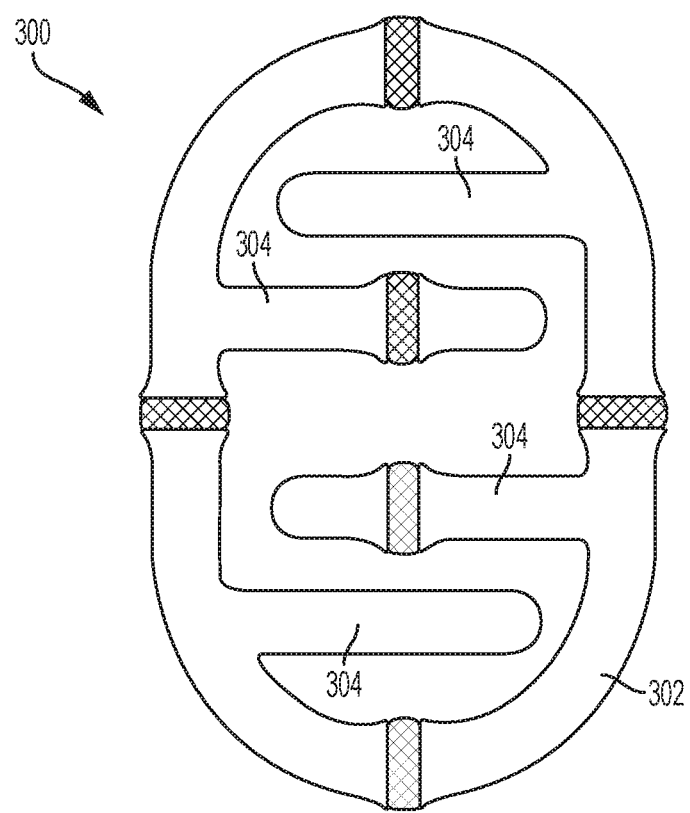
Figure 12C:
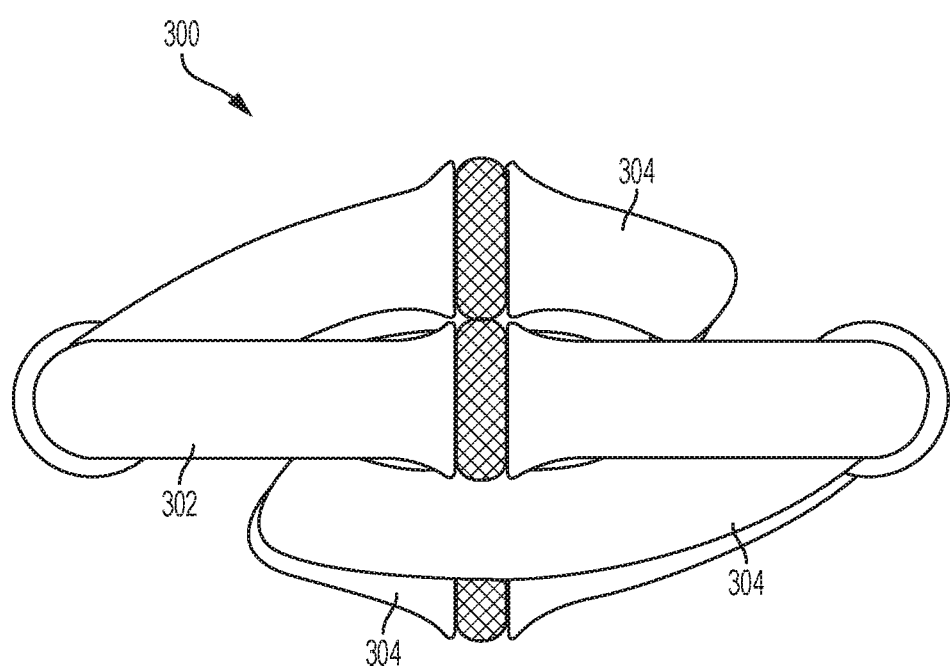
Figure 13:
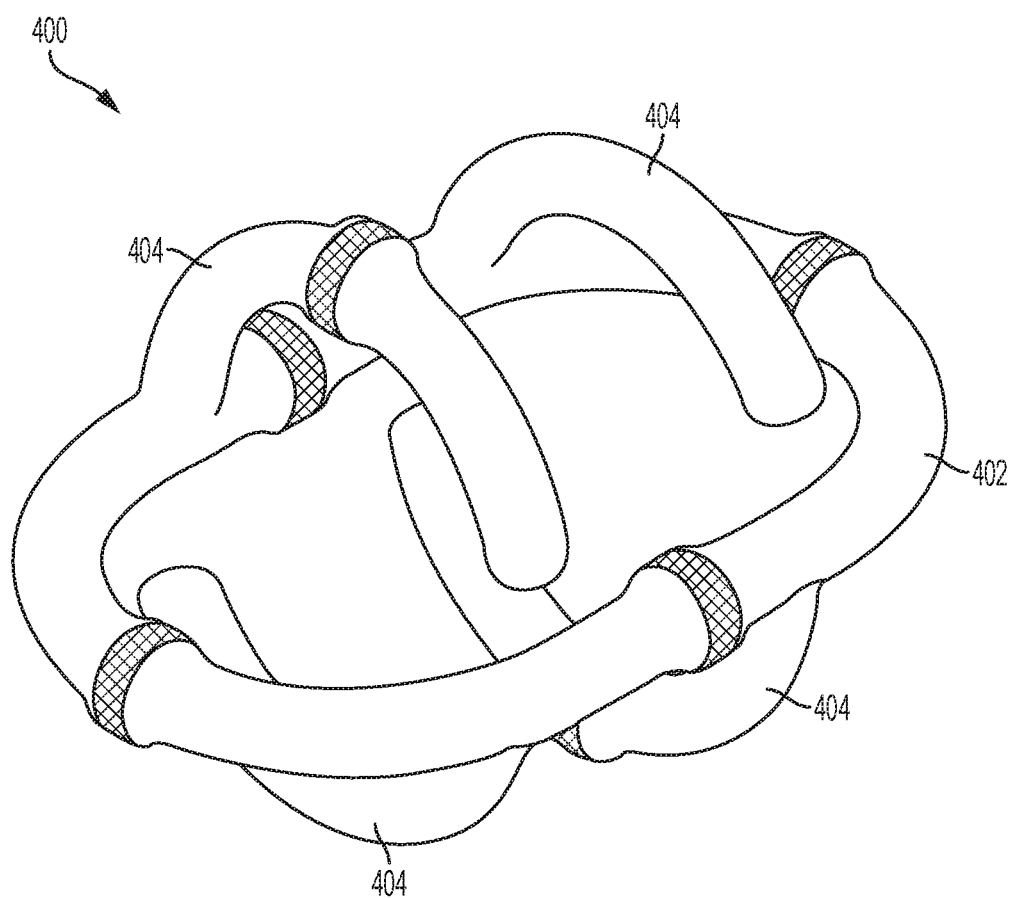

Additional variations of the oncoplastic device are provided in FIGS. 11-13. Perspective views of these figures illustrate various configurations of the framework elements and base elements of the devices. FIG. 11 shows an oncoplastic device (200) that is configured to include a circular base element (202) with opposing cantilevered cross-member elements (framework elements, 204). The framework elements (204) function as spacer elements and are configured to impart or provide the oncoplastic device with an overall profile (or three dimensional (3D) perimeter) in the form of an oblate ellipsoid of revolution. FIGS. 12A-12C show an oncoplastic device (300) that is configured to include an oval base element (302) with multiple (or an array of) cantilevered cross-member elements (framework elements, 304). The profile of the framework elements (302) and (304) correspondingly form a tri-axial ellipsoid. These cantilevered cross member elements (304) may appear straight when viewed from above (see FIG. 12B), but may be non-straight (e.g., arcuate, "dog-legged") in shape (e.g., when viewed from the side) (see FIG. 12C) to provide additional height in the transverse direction (orthogonal to the general plane of the base). As can be seen in FIG. 12B, the cross-member elements may or may not have radiopaque marker elements attached to them. An important function of the cross-member is to prevent opposing tissue surfaces from contacting each other during the healing process, thereby minimizing the growth of scar tissue at that location. FIG. 13 shows another oncoplastic device (400) structured to include an oval base element (402) with multiple cantilevered cross-member elements (framework elements, 404) that impart an overall profile to the device (400) that takes the form of a tri-axial ellipsoid. In this variation, the cantilevered cross-member elements (404) are of greater height than the analogous elements of the variation in FIGS. 12A-12C, thereby providing greater tissue separation of potential spaces or providing for the accommodation of larger tissue cavities.

Figure 14:
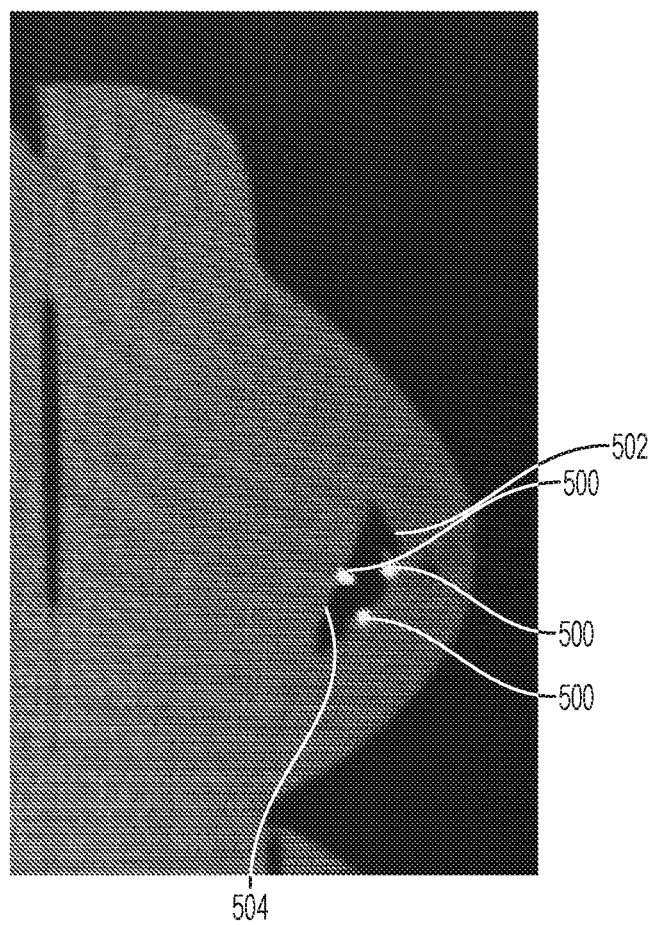
FIG. 14 shows a CT cross sectional image of the oncoplastic device of the type shown in FIG. 11 in a simulated breast surgery tissue environment.

FIG. 14 shows a CT cross-sectional image of the oncoplastic device of the type shown in FIG. 11 in a simulated breast surgery tissue environment. In this figure, a potential space was created in the soft simulated breast tissue via sharp dissection and then a device of the type shown in FIG. 11 was placed in the potential space between the two exposed dissected surfaces. As shown in the figure, the device may provide visualization of the tissue cavity region via the markers (500) but also note that the device holds apart the dissected tissue surfaces (502 and 504) from the opposing side of the cavity. In actual post-surgical healing breast tissue, the device may provide a similar function of holding apart opposing dissected tissue surfaces, a function which can minimize scarring during healing. As the physiologic healing process becomes less active with time post operatively, the structural (bioabsorbable) portion of the device may degrade and be absorbed naturally by the body. Reduced scarring during healing can improve the contour of the breast and can improve visibility of the breast tissue during follow-up mammography.

The devices described herein may be differentiated from implantable elements used for aesthetic or prosthetic reconstruction such as permanent implants (for example, for the breast or chin) as the disclosed devices provide a temporary structure that enables the surgeon to use the patient's own tissues to reconstruct and minimize anatomic deformities or irregularities that would otherwise be caused by the surgical removal of tissue. In addition, the external perimeter surface of these devices is generally non-contiguous as compared to a typical prosthetic breast implant, which has a contiguous surface. Rather, the devices disclosed herein are based upon an open framework rather than a closed contiguous framework. The bioabsorbable nature of the implant absorbs slowly during the healing process, but maintains its structural integrity while it is supporting the surrounding tissue flaps as they heal in place and reconstitute the size, shape, form and/or contour of the surgical area. They may be used at the time of surgical removal, or may be inserted into an area previously deformed by a surgical intervention (e.g., used at a later time following excision of tissue after a deformity has occurred due to seroma resorption and subsequent fibrotic scarring).

Furthermore, after a given period of time (e.g., after the tissue healing response is complete), the bulk of the device is resorbed by the body, leaving behind the tissue that has grown into or moved into the original region of tissue removal, as well as leaving behind any permanent radiographically visible elements. This attribute can contribute to reduced scarring, minimal contour deformities, as well as contribute to reconstruction, reconstitution of, or preservation of prior contour, shape and size of the original anatomic region. By providing support to the tissues underneath the surgical wound, the devices allow the subcutaneous tissues and in particular the subcutaneous and/or dermal lymphatics to heal in a more efficient and direct manner, thereby decreasing the amount of post-surgical swelling (edema), and allowing for expedited and improved healing and overall improved aesthetic/cosmetic appearance. Also, prior to complete degradation of the bioabsorbable element(s), the radiographic elements are held in their three-dimensional array during the tissue healing process, limiting their migration from their original surgically placed positions.

As further described below, the devices may be configured to allow for tissue to be incorporated into the open framework, by way of suturing or other attachment methods (e.g., surgical clips, wires, etc.). The tissue may be mobilized (detached) from overlying skin and surrounding tissues in order to secure the tissue to the open framework. One way this mobilization can be achieved in breast surgery is by surgically dissecting breast tissue along the mastectomy plane, a relatively avascular plane of tissue that lies deep to the dermal layers to create a flap, which can then be mobilized and secured to the framework of the oncoplastic device. The tissue can be secured in many different ways to the device, and in particular the design of the device may allow the surgeon to customize how local reconstruction of the area is accomplished in order to avoid anatomic irregularities. The device can be used to reconstruct the area or otherwise improve the contour of the region surrounding the tissue that was removed during the surgical procedure. Such tissues might include anything that is concerning, troublesome, suspicious for cancer, or has a known biopsy-proven cancer requiring removal. This can be glandular tissue (e.g. breast, prostate) subcutaneous tissue (fat and fibrous tissue) and other soft tissue structures (e.g. muscle). The devices described herein may allow the surgeon to rearrange adjacent tissue to reconstitute and/or reconstruct the region that was excised. Accordingly, breast reconstruction for partial mastectomy and mastopexy may be facilitated by using a temporary bioabsorbable open framework breast implant.

Methods

Figure 9A:
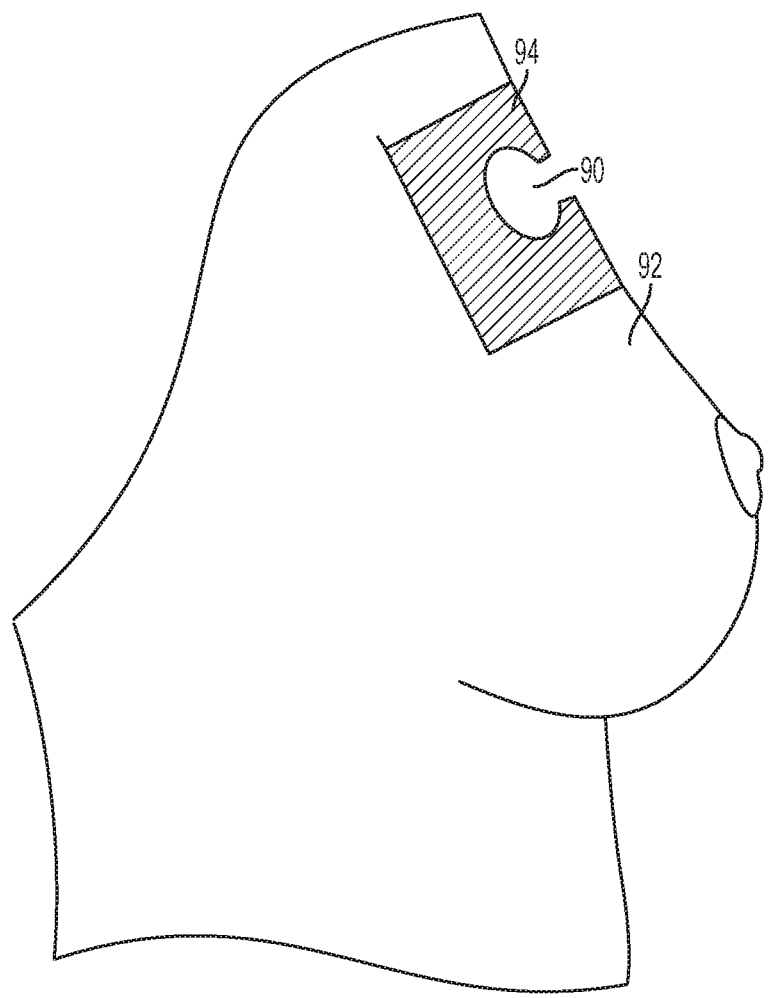
FIGS. 9A-9D illustrate various methods by which breast tissue adjacent to the surgically created cavity can be manipulated using an exemplary oncoplastic device.

The methods of breast surgery described herein generally include the steps of removing breast tissue to create a cavity, placing an oncoplastic device into the cavity, the oncoplastic device comprising a body having an open framework formed of a bioabsorbable material and having an anterior, posterior, and lateral regions, manipulating tissue surrounding the cavity, and attaching (e.g., via suture) the open framework of the oncoplastic device to the manipulated tissue, as illustrated in FIGS. 9A-9D and 10. An exemplary surgically created cavity (90) in breast tissue (92), and tissues (94) (shaded area) surrounding the cavity (90) are shown in FIG. 9A. The manipulation of tissue may comprise tissue flap creation, moving, displacing, mobilizing, or dissecting tissue (including skin) in the proximity of the removed tissue (including the tissue surrounding a cavity). Alternatively, the manipulation of tissue may include approximation of tissues to or within the open framework. In some instances, it is useful at the time of surgery to perform tissue manipulation before, during, or after placing the oncoplastic device into the cavity. In other instances it is useful to perform tissue manipulation before, during, or after securing elements (e.g., framework elements) of the open framework of the oncoplastic device to the tissue. In yet further instances, it may be useful to place a cavity sizing instrument in the cavity prior to selection of the proper size of oncoplastic device and placement of the oncoplastic device.

Some variations of the method include removing an area of breast tissue to create a cavity, an opening, or a space; placing an oncoplastic device into the cavity, the opening, or the space, the oncoplastic device comprising a body having an open framework and formed of a bioabsorbable material, the open framework comprising an anterior, a posterior, and lateral regions, and an array of cross-member elements that impart an ellipsoid profile to the open framework; manipulating tissue surrounding the cavity, the opening, or the space; and attaching the open framework to the manipulated tissue.

In other variations, the method may be used in a breast lumpectomy procedure including all or some of the following steps: a lumpectomy cavity is created by surgically removing breast tissue via a carefully designed and contoured, cosmetically chosen skin incision that may be distinctly different from the site of the tissue removal (e.g., which may include tunneling from a circumareolar incision); the cavity is sized using a sizer and/or other sizing methods (e.g., direct examination of the lumpectomy specimen or cavity); estimating the location, size, shape and orientation of the tumor; placing an appropriately sized three-dimensional open architecture bioabsorbable tissue marker (implanted) directly into the lumpectomy cavity (preferably using a device size, shape, and location that corresponds to the size, shape, location and/or orientation of the tumor site) via the surgical incision causing the breast tissue at the margin of the cavity to actively (e.g., via suture closure) or passively insinuate or otherwise move across the peripheral boundary of the device; closing the surgical site via single or multiple layered closure techniques; and then closing the skin. Creation and mobilization of tissue flaps may be performed at any time during the above-described procedure, prior to skin closure.

Alternatively, the device may be used as above but with the added step of passing suture around one or more portions of the device and then passing the suture through adjacent tissue to tether or otherwise further secure the device to the adjacent tissue.

Figure 9B:
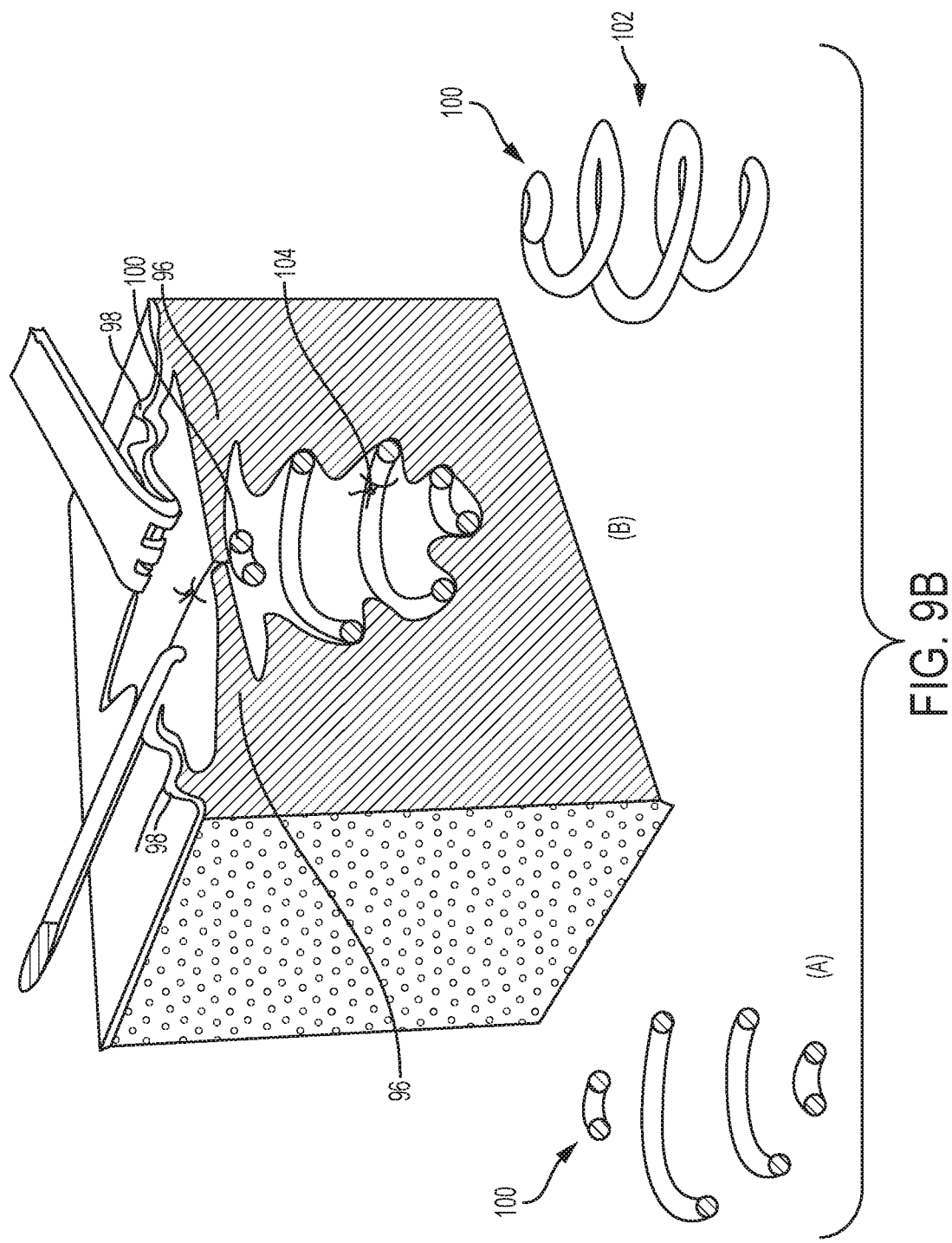

In one variation, as shown in FIG. 9B, the manipulation of tissue includes forming tissue flaps (96) by dissection beneath the skin (98) and draping the flaps (96) over an anterior region (100) of an oncoplastic device (102), in a manner somewhat analogous to an awning or tent. Although a spiral-shaped device is shown in the figure, it is understood that any oncoplastic device described herein may be implanted. Cross-sectional views of the device (A) and device implanted within the cavity (B) are shown to provide further understanding of how the tissues may be manipulated and attached using the device. Again, FIG. 9B depicts closure of the tissue flaps (96) over an anterior region (100) of oncoplastic device (102). This closure of tissue layers beneath the skin, e.g., by suturing may help to prevent dimpling or divoting of the skin overlying the cavity, and thus preserve the natural contour of the breast. The oncoplastic device (102) is also secured to the tissue surrounding the cavity at other locations desired by the surgeon, (e.g., lateral attachment point (104)).

Figure 9C:
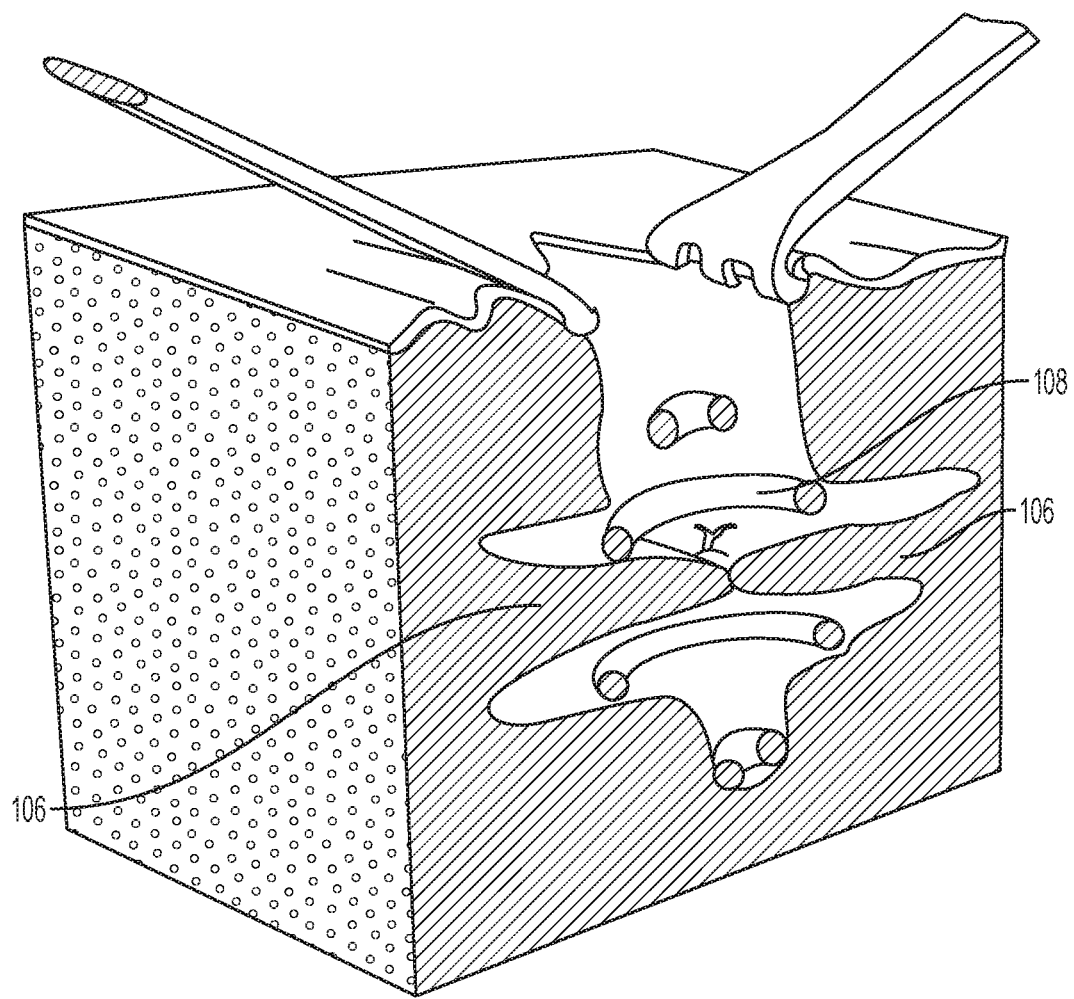
Figure 10:
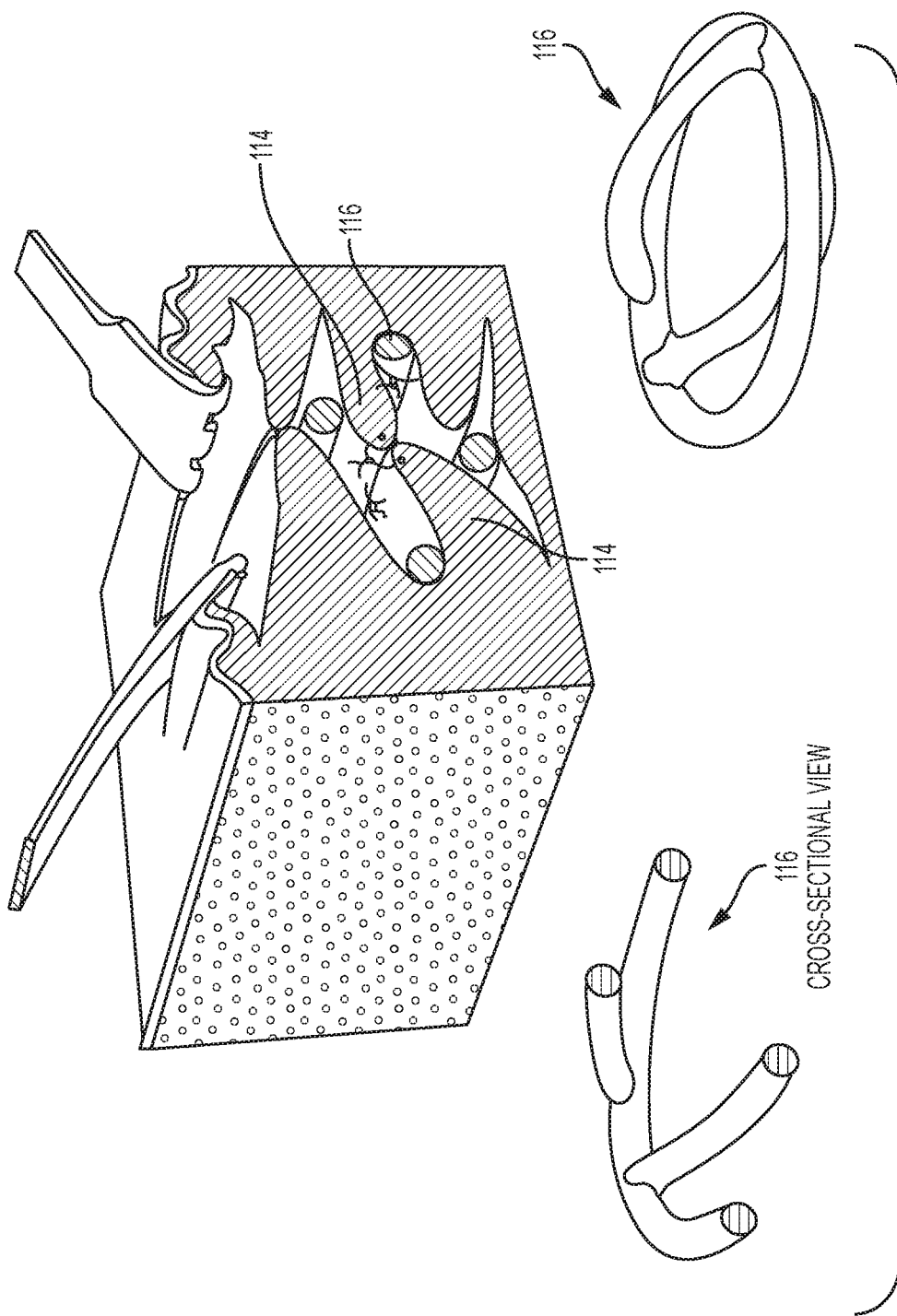
FIG. 10 illustrates another variation of the method by which breast tissue adjacent to the surgically created cavity can be manipulated using other exemplary devices.

In other variations, the tissues can be mobilized and/or integrated within the device and sutured to the device at various locations through the device or along various aspects of its structural elements. The tissues may be attached to the perimeter (superior, inferior, lateral, medial) regions of the device with the device being used as a "bridge" to decrease tension on an area of tissue closure. For example, as shown in FIGS. 9C and 10, tissue surrounding the cavity, e.g., tissue flaps (106, 114) can be pulled through the device (102, 116) and secured together.

Figure 9D:
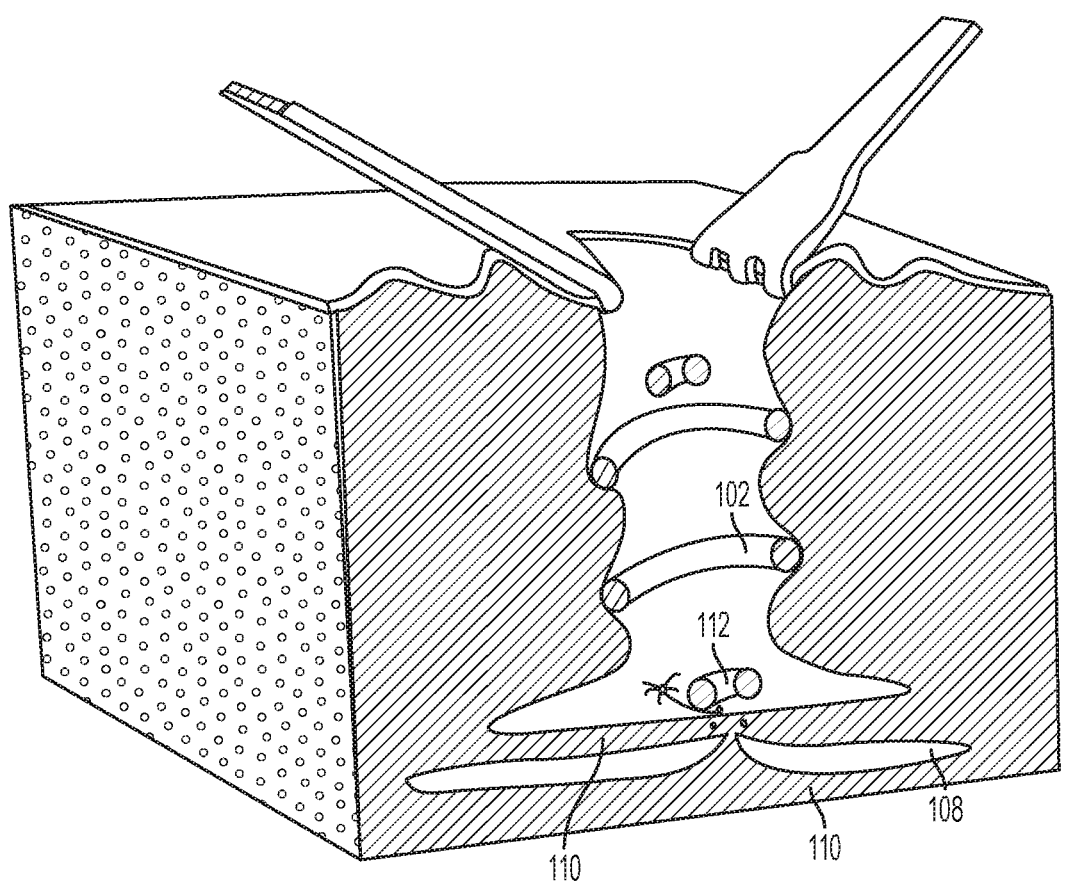

Tissues may alternatively be connected to posterior regions of a device, as shown in FIG. 9D. Referring to the figure, device (102) is used to help close the posterior aspect of cavity (108). Specifically, tissues (110) that lie posterior to the device (102) are attached to a posterior region (112) of the device (102). In many cases a combination of these approaches can be used in a single patient. These are just a few examples of how the tissues may be secured to the device in a fashion that envelopes tissue around, or integrates tissue within the device in order to minimize the undesirable contour effects that the original tissue/tumor removal would otherwise have had on the surgical area.

The methods and devices described herein generally enable surgeons to mobilize tissues into a region where they have removed tissue, and that would otherwise cause a void, fill with seroma fluid after surgery, and ultimately create an anatomic deformity or irregularity. It facilitates learning and practice in the field of oncoplastic surgery, which can be described as combining the principles, philosophy, and techniques of surgical oncology (adequate tissue removal with an adequate margin), with the principles, philosophy, and techniques of aesthetic and reconstructive surgery. The ability to perform oncoplastic surgery in this manner may be facilitated by the device because it holds the tissues in place during healing, since the tissues are secured directly to the device. This allows the surgeon to suture the adjacent tissues (particularly after mobilization) to the device and support the tissues during healing, thereby preserving the contour, shape, and size of an anatomic location such as the breast. In addition, tissues may also be wrapped entirely or in part around the periphery of the device so as to envelope the entirety or portions of the device.

The invention claimed is:

1. A method of treating cancer in a partial breast reconstruction, the method comprising:
   placing an oncoplastic device within a cavity or space, the cavity or space formed by surgical removal of tissue, wherein the oncoplastic device comprises:
   an open framework body formed by one or more framework elements, wherein the one or more framework elements are configured to provide structural support to the tissue forming the cavity or space and allow seroma fluid to pass through the open framework body so that the seroma fluid can promote tissue regrowth within the open framework body of the oncoplastic device to at least partially reconstruct a breast; and
   a therapeutic drug for treatment of cancer, or to improve tissue healing, or to prevent infection, or a combination thereof;
   dissecting tissue situated under dermal layers of a patient's skin to create one or more tissue flaps in the tissue forming the cavity or space; and
   draping the one or more tissue flaps over the open framework body.

2. The method of claim 1, wherein the therapeutic drug is contained within a plurality of discrete elements spaced about the open framework body.

3. The method of claim 2, wherein the plurality of discrete elements are symmetrically spaced about the open framework body.

4. The method of claim 2, wherein the plurality of discrete elements are asymmetrically spaced about the open framework body.

5. The method of claim 2, wherein the plurality of discrete elements further assist in delineating a three-dimensional region of tissue for subsequent clinical imaging.

6. The method of claim 2, wherein the plurality of discrete elements further serve as fiducial markers.

7. The method of claim 1, wherein the open framework body further includes a plurality of discrete radiographically visible elements spaced thereon.

8. The method of claim 1, further comprising attaching the dissected tissue to the oncoplastic device.

9. The method of claim 8, wherein attaching the dissected tissue to the oncoplastic device comprises one of:
   pulling the dissected tissue through the open framework body;
   suturing the dissected tissue through the open framework body;
   wrapping the dissected tissue around the open framework body; and
   suturing the dissected tissue to the open framework body.

10. The method of claim 1, wherein after placement of the oncoplastic device, the open framework body has a flattened or low profile-shape.

11. The method of claim 1, wherein, after placement of the oncoplastic device, a height of the open framework body is substantially less than a width and a length of the open framework body.

12. The method of claim 1, wherein the one or more framework elements comprise a single, U-shaped framework element.

13. The method of claim 1, wherein the one or more framework elements comprise a plurality of framework elements.

14. The method of claim 13, wherein the plurality of framework elements comprises a circular or ovoid base element and one or more curved or arcuate spacer elements.

15. The method of claim 1, wherein draping the one or more tissue flaps over the open framework body comprises draping the one or more tissue flaps over an anterior region of the open framework body.

16. The method of claim 1, wherein the open framework body comprises one unitary framework element comprised of a spiral-shape.

17. A method of treating cancer in a partial breast reconstruction, the method comprising:
   placing an oncoplastic device within a cavity or space, the cavity or space being formed by surgical removal of tissue of a breast, the oncoplastic device comprising an open framework body formed of a bioabsorbable material;
   forming one or more tissue flaps in subcutaneous tissue defining the cavity or space;
   draping the one or more tissue flaps over the open framework body; and
   restoring a contour of the breast by supporting the one or more tissue flaps with the open framework body, while allowing seroma fluid to pass through the open framework body so that the seroma fluid can promote tissue regrowth within the open framework body.

18. The method of claim 17, further comprising supporting the tissue defining the cavity or space with the open framework body.

19. The method of claim 18, further comprising attaching surrounding tissue of the cavity or space to the open framework body.

20. The method of claim 19, wherein attaching the surrounding tissue of the cavity or space to the open framework body comprises one of:
   pulling the surrounding tissue through the open framework body;
   suturing the surrounding tissue through the open framework body;
   wrapping the surrounding tissue around the open framework body; and
   suturing the tissue to the open framework body.

21. The method of claim 17, further comprising providing cancer treatment to the breast via a therapeutic drug in the open framework body.

22. The method of claim 17, wherein placing the oncoplastic device within the cavity or space comprises placing the oncoplastic device within a cavity or space having minimal overlying tissue.

23. The method of claim 22, wherein, after placement of the oncoplastic device, a height of the open framework body is substantially less than a width and a length of the open framework body.

24. The method of claim 17, wherein forming the one or more tissue flaps in the tissue defining the cavity or space comprises surgically dissecting breast tissue along a mastectomy plane.

25. A method of treating cancer in a partial breast reconstruction, the method comprising:
   placing an oncoplastic device within a cavity or space, the cavity or space being formed by surgical removal of tissue of a breast, the oncoplastic device comprising an open framework body formed of a bioabsorbable material;
   forming one or more tissue flaps in tissue surrounding the cavity or space;
   draping the one or more tissue flaps over the open framework body;
   attaching the one or more tissue flaps to the open framework body by pulling the tissue flaps through the open framework body, suturing the tissue flaps through the open framework body, wrapping the tissue flaps around the open framework body, and/or suturing the tissue flaps to the open framework body; and restoring a contour of the breast by supporting the one or more tissue flaps with the open framework body, while allowing seroma fluid to pass through the open framework body so that the seroma fluid can promote tissue regrowth within the open framework body.

\* \* \* \* \*